US012746329B2

(12) United States Patent
Dave et al.

(10) Patent No.: US 12,746,329 B2
(45) **Date of Patent: *Sep. 29, 2026**

(54) DRUG DELIVERY DEVICE ACTUATED USING LEAD SCREW AND MOTOR

(71) Applicant: Manta MedTech LLC, Newark, DE (US)

(72) Inventors: Raju S. Dave, Gaithersburg, MD (US); Xing Su, Santa Clara, CA (US); Himanshu Verma, McLean, VA (US); Ashish Shah, East Amherst, NY (US); Kenta Alten, Los Altos Hills, CA (US); Krishna Chittur Ranganathan Shastri, Thane (IN)

(73) Assignee: Manta MedTech LLC

( * ) Notice: Subject to any disclaimer, the term of this patent is extended or adjusted under 35 U.S.C. 154(b) by 0 days.

This patent is subject to a terminal disclaimer.

(21) Appl. No.: 19/264,486

(22) Filed: Jul. 9, 2025

(65) Prior Publication Data

US 2026/0102561 A1 Apr. 16, 2026

Related U.S. Application Data

(63) Continuation-in-part of application No. 19/006,338, filed on Dec. 31, 2024.

(Continued)

(51) Int. Cl.

| | |
|---|---|
| ***A61M 5/145*** | (2006.01) |
| ***A61M 5/14*** | (2006.01) |
| ***A61M 5/142*** | (2006.01) |

(52) U.S. Cl.

CPC ...... *A61M 5/14526* (2013.01); *A61M 5/1409* (2013.01); *A61M 5/14248* (2013.01);

(Continued)

(58) Field of Classification Search

CPC ............ A61M 5/14526; A61M 5/1409; A61M 5/14248; A61M 2202/0007;

(Continued)

(56) References Cited

U.S. PATENT DOCUMENTS

2009/0259217 A1 10/2009 Hyde et al.
2012/0059349 A1 3/2012 Kuo et al.

(Continued)

*Primary Examiner* — Cris L. Rodriguez

(74) *Attorney, Agent, or Firm* — Davé Law Group, LLC; Raj S. Davé

(57) ABSTRACT

A system is described. The system comprises an active wearable medical device (AWMD), a fluid chamber, and a channel for delivering a drug. The AWMD comprises a drug chamber, a motor chamber, a piston, an electronic module, and a permeability module. The motor chamber comprises a motor, and a driving component. The piston is affixed to an end of the driving component. The electronic module actuates the motor to operate the driving component and move the piston longitudinally to discharge a drug outside through orifices. The permeability module allows passive ingress of a fluid to an osmotic chamber from the fluid chamber through a semipermeable membrane and generates osmotic pressure to drive the piston longitudinally in addition to actuation by the motor. The AWMD is not implanted in a body of a mammal and is fluidically coupled to the fluid chamber via the semipermeable membrane.

20 Claims, 18 Drawing Sheets

Related U.S. Application Data

(60) Provisional application No. 63/707,896, filed on Oct. 16, 2024.

(52) U.S. Cl.
CPC ............... *A61M 2202/0007* (2013.01); *A61M 2205/0216* (2013.01); *A61M 2205/3327* (2013.01); *A61M 2205/3331* (2013.01); *A61M 2205/50* (2013.01); *A61M 2209/088* (2013.01); *A61M 2210/04* (2013.01)

(58) Field of Classification Search
CPC .. A61M 2205/0216; A61M 2205/3327; A61M 2205/3331; A61M 2205/50; A61M 2209/088; A61M 2210/04; A61M 5/16804; A61M 39/24; A61M 2005/14513; A61M 2205/04; A61M 2205/18; A61M 2205/3303; A61M 2205/3576; A61M 2205/75; A61M 2230/005
See application file for complete search history.

(56) References Cited

U.S. PATENT DOCUMENTS

| | | | | |
|---|---|---|---|---|
| 2017/0189609 A1* | 7/2017 | Wei | ................... | A61M 5/14526 |
| 2021/0283330 A1 | 9/2021 | Mayse | | |
| 2024/0016728 A1* | 1/2024 | Mitsuoka | .......... | A61M 5/31513 |
| 2025/0205418 A1* | 6/2025 | Yoshikawa | .......... | A61K 9/0004 |

* cited by examiner

DRUG DELIVERY DEVICE ACTUATED USING LEAD SCREW AND MOTOR

CROSS REFERENCE TO RELATED APPLICATIONS

This application is a Continuation-in-Part application of U.S. patent application Ser. No. 19/006,338, filed Dec. 31, 2024, titled "IMPLANTABLE DEVICE ACTUATED USING LEAD SCREW AND MOTOR," which claims the benefit of priority of U.S. Patent Application No. 63/707,896, filed dated 16 Oct. 2024 and titled "DEVICE BASED TREATMENTS FOR SUBSTANCE USE DISORDERS", the content of which is incorporated herein by reference in its entirety.

TECHNICAL FIELD

This disclosure relates to a drug delivery system, and more specifically relates to an active wearable medical device (AWMD) that actuates a piston longitudinally using both an osmotic pressure and a motor.

BACKGROUND ART

Poor medication adherence is a significant issue, leading to numerous hospital admissions and high healthcare costs. Factors contributing to nonadherence include poor insight, substance abuse, negative attitudes, side effects, and cognitive impairments. This problem is exacerbated among older adults on multiple medications, resulting in worsened health outcomes and increased mortality. Additionally, drug overdoses, particularly opioid-related, remain a severe public health crisis in the U.S., causing significant loss of life and economic burden.

Considering knowledge of a person skilled in the art, there is a long-felt need to address the shortcomings in the prior art and provide a system that is capable of implementing comprehensive strategies addressing issues related to clinical efficacy, toxicity, drug properties, and personalized drug dosing. It would be advantageous to have a system, method and device that considers at least some of the issues discussed above, as well as possibly other issues.

SUMMARY OF INVENTION

The following paragraphs present a summary to provide a basic understanding of one or more embodiments described herein. This summary is not intended to identify key or critical elements or delineate any scope of the different embodiments and/or any scope of the claims. The sole purpose of the summary is to present some concepts in a simplified form as a prelude to the more detailed description presented herein.

Embodiments relate to an active implantable medical device (AIMD). The AIMD comprises a drug chamber, a motor chamber, a piston, and an electronic module. The drug chamber comprises a drug. The motor chamber comprises a housing, a motor, and a driving component. The motor may be a stepper motor. The driving component is coupled to the motor such that when the motor is operated the driving component also rotates. The driving component may be a helical threaded screw which converts the rotational motion to a linear motion. The piston is affixed to a first end of the driving component. The first end is an end which is towards one or more orifices through which the drug is discharged from the AIMD to outside the AIMD (i.e., a subject). As the piston is affixed to the first end of the driving component, the piston moves longitudinally towards the one or more orifices, which discharges the drug from the drug chamber to the subject (i.e., outside the AIMD). The subject may be a living being (e.g., a human, animal, a mammal, etc.).

The active implantable medical device (AIMD) may comprise a sensor module and an electronic module. The sensor module is configured to measure displacement of a piston. The electronic module communicates a signal to the stepper motor to control the stepper motor and regulate the one-way flow of the drug based on the displacement of the piston precisely and accurately. Additionally, the electronic module comprises a power supply module for supplying energy to the electronics module, the sensor module, and the motor. The device is designed with a tubular structure for subcutaneous implantation. The device releases the drug, while the sensor module monitors relevant parameters, for example, displacement. A communication web connects all modules, ensuring the synchronized movement of the piston towards the drug chamber with each release, with motor the actuating this action and the sensor detecting the piston's movement.

In an aspect, an active implantable medical device (AIMD) is described. The AIMD comprises: a drug chamber that comprises a drug; a motor chamber that comprises a housing, a motor, and a driving component; a piston that is affixed to a first end of the driving component; and an electronic module that actuates the motor to operate the driving component and move the piston longitudinally to discharge the drug outside the AIMD through one or more orifices.

In some embodiments, the driving component comprises a helical threaded screw. A first length of the driving component is equal to the sum of a second length of the motor, a third length between an initial position of the piston and a motor position, and a fourth length between the initial position of the piston and a displacement position of the piston.

The AIMD may comprise a check valve coupled to the one or more orifices. The check valve allows one-way flow of the drug from the drug chamber to outside the AIMD through the one or more orifices. The check valve blocks entry of a fluid to the drug chamber from outside the AIMD. The check valve remains closed until the incoming pressure reaches a threshold pressure.

In some embodiments, the piston and the driving component moves together longitudinally to discharge the drug upon actuating the motor. An outer circumference of the piston is in surface compliance with the AIMD to prevent leakage or contamination.

The AIMD comprises a sensor module. In an embodiment, the sensor module monitors one or more physiological parameters of a subject. The sensor module communicates a signal to the electronic module when the one or more physiological parameters of the subject is abnormal. The sensor module may communicate a signal to the electronic module at a prescribed time. The electronic module may actuate the motor in response to a signal received from the sensor module.

In some embodiments, an outer circumference of the piston comprises a sealing component. The sealing component prevents leakage of the drug from the drug chamber to the motor chamber. The sealing component prevents contamination of the drug in the drug chamber with a fluid or gas in the motor chamber.

In some embodiments, the motor chamber is configured to pressurize a gas within the motor chamber of the AIMD. The pressurization of the gas restricts creation of vacuum within the AIMD when the piston moves longitudinally towards the one or more orifices. The gas may be an inert gas.

In some embodiments, the housing of the motor chamber comprises a permeability module. The permeability module comprises a semipermeable membrane and an osmotic agent chamber. The permeability module allows ingress flow of a fluid to an osmotic agent chamber and generates osmotic pressure. The osmotic pressure drives the piston to move longitudinally towards the one or more orifices in addition to the actuation of the motor. The osmotic pressure is directly proportionate to the movement of the piston longitudinally. The ingress flow of the fluid controls the discharge of the drug.

In some embodiments, the housing of the motor chamber comprises one or more provisions and a filter. The one or more provisions allows ingress flow of a fluid from outside the AIMD to the motor chamber through the filter. The ingress flow of the fluid from outside the AIMD to the motor chamber prevents creation of vacuum within the AIMD.

In an embodiment, the electronic module comprises a microprocessor.

In another aspect, an active implantable medical device (AIMD) is described. The AIMD comprises: a drug chamber that comprises a drug; a motor chamber that comprises a housing, a motor, and a driving component; a stationary guiding component comprising a provision through which the driving component protrudes longitudinally; and an electronic module that actuates the motor to operate the driving component and protrude longitudinally through the stationary guiding component to discharge the drug outside the AIMD through one or more orifices. The electronic module may comprise a microprocessor. The AIMD may comprise a sealing component between the stationary guiding component and the driving component.

The driving component may comprise a flattened surface at a first end to push the drug through the one or more orifices. An outer circumference of the flattened surface is in surface compliance with the AIMD. The driving component is operable to function as a piston to discharge the drug outside the AIMD through one or more orifices. The driving component comprises a helical threaded screw. The length of the driving component is equal to the sum of a length of the motor, a length between an initial position of the first end of the driving component and a motor position, and a length between the initial position of the first end of the driving component and a displacement position of the first end of the driving component. The stationary guiding component comprises one or more bumps configured to prevent rotation of the stationary guiding component. An outer circumference of the stationary guiding component comprises a sealing component. The sealing component prevents leakage of the drug from the drug chamber to the motor chamber. The sealing component prevents contamination of the drug in the drug chamber with a fluid or gas in the motor chamber.

The AIMD may comprise a check valve coupled to the one or more orifices. The check valve allows one-way flow of the drug from the drug chamber to outside the AIMD through the one or more orifices. The check valve blocks entry of a fluid to the drug chamber from outside the AIMD.

The AIMD comprises a sensor module. The sensor module monitors one or more physiological parameters of a subject. The sensor module communicates a signal to the electronic module when the one or more physiological parameters of the subject is abnormal. The sensor module communicates a signal to the electronic module at a prescribed time. The electronic module actuates the motor in response to a signal received from the sensor module.

In some embodiments, the motor chamber is configured to pressurize a gas within the motor chamber of the AIMD. The pressurization of the gas restricts creation of vacuum within the AIMD when the driving component moves longitudinally towards the one or more orifices. The gas may be an inert gas.

In some embodiments, the housing of the motor chamber comprises a permeability module. The permeability module comprises a semipermeable membrane and an osmotic agent chamber. The permeability module allows ingress flow of a fluid to an osmotic agent chamber and generates osmotic pressure. The osmotic pressure pushes the driving component to move longitudinally towards the one or more orifices in addition to the actuation of the motor. The osmotic pressure is directly proportionate to the movement of the driving component longitudinally. The ingress flow of the fluid controls the discharge of the drug.

In some embodiments, the housing of the motor chamber comprises one or more provisions and a filter. The one or more provisions allows ingress flow of a fluid from outside the AIMD to the motor chamber through the filter. The ingress flow of the fluid from outside the AIMD to the motor chamber prevents creation of vacuum within the AIMD.

In another aspect, a method is described. The method comprises: monitoring one or more physiological parameters of a subject using a sensor module; communicating a signal to an electronic module when the one or more physiological parameters is abnormal; and actuating a motor using the electronic module based on the signal to operate a driving component and move a piston longitudinally to discharge a drug to a subject outside an active implantable medical device (AIMD) through one or more orifices. The sensor module may be placed within the subject. The sensor module is communicatively coupled to the AIMD.

In another aspect, a system is described. The system comprises (1) an active wearable medical device (AWMD), (2) a fluid chamber, and (3) a channel. The active wearable medical device (AWMD) comprises at least one drug chamber, a motor chamber, a piston, an electronic module, and a permeability module. The at least one drug chamber comprises a drug. The motor chamber comprises a housing, a motor, and a driving component. The piston is affixed to a first end of the driving component. The electronic module actuates the motor to operate the driving component and move the piston longitudinally to discharge the drug outside the active wearable medical device (AWMD) through one or more orifices. The permeability module allows passive ingress flow of a fluid from a fluid chamber to an osmotic agent chamber through a semipermeable membrane upon activation of the fluid chamber and generates osmotic pressure to drive the piston longitudinally towards the one or more orifices in addition to actuation of the piston by the motor. The fluid chamber contains the fluid and is fluidically coupled to the active wearable medical device (AWMD) via the semipermeable membrane. The channel is fluidically coupled to a drug outlet wherein the channel discharges and deliver the drug. According to an embodiment, the active wearable medical device (AWMD) is not implanted in a body of a mammal.

In an embodiment, the fluid chamber is an expandable elastomeric bladder that expands and gradually releases the fluid across the semipermeable membrane to generate the osmotic pressure when a pressure is applied to the expandable elastomeric bladder.

In another embodiment, the fluid chamber is a rigid reservoir that enables diffusion of the fluid across the semi-permeable membrane to dissolve an osmotic agent in the osmotic agent chamber and generate an osmotic gradient to drive the piston.

In another embodiment, the fluid chamber is a hydrogel reservoir.

In another embodiment, the hydrogel reservoir comprises a hydrogel that releases the fluid over time to enable the passive ingress flow of the fluid to the osmotic agent chamber from the hydrogel reservoir.

In another embodiment, the fluid chamber is a microfluidic reservoir.

In another embodiment, the microfluidic reservoir is integrated with a flow restrictor interfaced with the semi-permeable membrane to deliver the fluid to the osmotic agent chamber at a controlled rate.

In another embodiment, the fluid chamber is an active operated chamber.

In another embodiment, the fluid chamber is a passive operated chamber.

In another embodiment, the channel comprises a catheter configured to deliver the drug to a specific anatomical site.

In another embodiment, the catheter is configured for targeted administration of the drug.

In another embodiment, the system comprises an attachment component having perforations adapted to secure the system to skin and to ensure stable contact with the skin during the discharge of the drug.

In another embodiment, the channel comprises a biocompatible material.

In another embodiment, the system comprises a plurality of drug chambers.

In another embodiment, the system is configured via the electronic module to switch between the plurality of drug chambers for sequential discharge of the drug or combination of discharge of the drug.

In another embodiment, the channel comprises a dissolvable material that naturally dissolves in the body over a period of time.

In another embodiment, the system comprises a real-time imaging and navigation guidance device.

In another embodiment, the real-time imaging and navigation guidance device is configured to aid placement of the catheter and monitor dispersion of the drug in real-time.

In another embodiment, the attachment component comprises an adhesive layer.

In another embodiment, the attachment component comprises one of a mechanical fastener, a wearable strap, a wearable band, and a skin micro-anchor.

The methods and systems disclosed herein may be implemented by any means necessary for achieving various aspects to perform any of the operations disclosed herein. Other features will be apparent from the accompanying drawings and from the detailed description that follows.

BRIEF DESCRIPTION OF DRAWINGS

These and other aspects of the present disclosure will now be described in more detail, with reference to the appended drawings showing exemplary embodiments of the present disclosure, in which.

Figure 1:
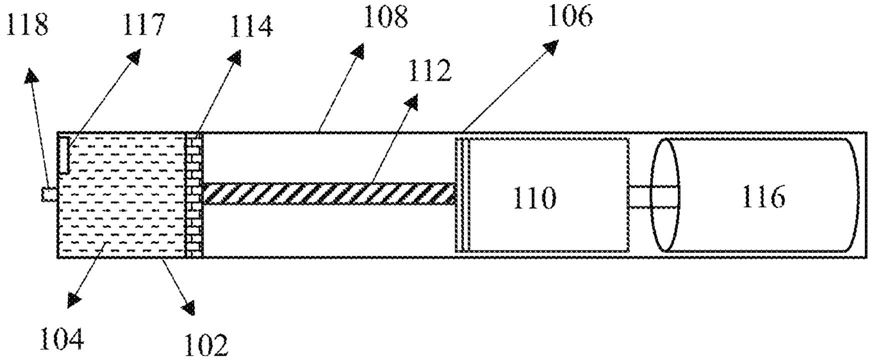
FIG. 1 illustrates an active implantable medical device (AIMD) comprising a lead screw and a motor for actuating a piston in longitudinal direction, according to one or more embodiments.

Other features of the present embodiments will be apparent from the accompanying drawings and from the detailed description that follows.

DESCRIPTION OF EMBODIMENTS

Definitions and General Techniques

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent, or semipermanent or only for an instant. "Electrical coupling" and the like should be broadly understood and include electrical coupling of all types. The absence of the word "removably," "removable," and the like near the word "coupled," and the like does not mean that the coupling, etc., in question is or is not removable.

As defined herein, two or more elements are "integral" if they are comprised of the same piece of material. As defined herein, two or more elements are "non-integral" if each is comprised of a different piece of material.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present disclosure may be embodied in other specific forms without departing from its spirit or characteristics. The embodiments described are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific, and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present disclosure are generally performed according to conventional methods well-known in the art and as described in various general and more specific references that are cited and discussed throughout the present specification unless otherwise indicated. The nomenclatures used in connection with, and the procedures and techniques of, embodiments herein, and other related fields described herein are those well-known and commonly used in the art.

The following terms and phrases, unless otherwise indicated, shall be understood to have the following meanings.

As used herein, the term "drug chamber" refers to a compartment, container, or enclosed space within the AIMD designed for the controlled storage, dispensing, or delivery of drugs or pharmaceutical substances.

As used herein, the term "motor chamber" refers to a housing or enclosure that contains a motor and related components. The motor chamber serves to protect the motor from environmental factors and ensure its proper functioning.

As used herein, the term "driving component" refers to a component that links the piston to a motor shaft. The driving component may comprise helical threaded region which converts the rotational motion to longitudinal motion and moves the piston longitudinally and discharges the drug outside the AIMD.

As used herein, the term "lead screw" also known as a power screw or translation screw, is a mechanical device used to convert rotational motion into linear motion. The screw has a helical thread that engages with a corresponding threaded nut, moving it along the axis of the screw. Lead screws come in various thread forms, for example trapezoidal, ACME, and square threads. Lead screws are used in applications requiring precise linear positioning.

As used herein, the term "medication" is defined as a substance or combination of substances or drug used to diagnose, treat, prevent, or alleviate symptoms of a disease or medical condition.

As used herein, the term "interstitial fluid" refers to a medium through which devices interact with the body. Interstitial fluid provides a direct interface between the device and the body. The AIMD relies on interstitial fluid for the diffusion of drugs into surrounding tissues. Interstitial fluid can act as a trigger or medium for dynamic responses in implantable devices. The interstitial fluid acts as a balancing agent, maintaining stable pressure within the device and enabling the piston to move forward without hindrance, ensuring precise and continuous medication delivery.

As used herein, the term "housing" refers to a protective enclosure or framework that surrounds and supports a component, device, or system. Its primary purpose is to shield the internal parts from external elements, provide structural integrity, and sometimes aid in heat dissipation, noise reduction, or aesthetic appeal.

As used herein, the term "piston" refers to a precision-engineered component to control the movement of fluids. Pistons are used to regulate the precise delivery of medication by moving in response to pressure changes or external controls.

As used herein, the term "electronic module" refers to a compact and integrated unit containing the electronic components and circuits required for the device to perform its functions. The electronic module is configured to perform control and processing, data storage, communication, and power management. The electronic module is designed considering the Hermetic Sealing to protect the electronics from body fluids and to ensure longevity.

As used herein, the term "helical thread" refers to a spiral-shaped groove or ridge that wraps around a surface of a component. It is a key feature of screws, bolts, and other threaded fasteners, as well as components like leadscrews or threaded pipes. Helical threads are adapted to convert rotational motion into linear motion, and to form a tight seal between components.

As used herein, the term "check valve" refers to a mechanical device designed to allow the flow of fluids (liquids or gases) in one direction only, preventing reverse flow. It is a type of non-return valve that operates automatically, relying on the pressure and flow of the fluid to open or close the valve. The check valve may be one of swing check valve, ball check valve, lift check valve, diaphragm check valve, and spring-loaded valve. The check valve involves minimal maintenance due to uncomplicated design. The check valve remains closed until the incoming pressure reaches a threshold pressure.

As used herein, the term "orifice" refers to a small, precisely sized opening or hole in a plate, pipe, or other structure, designed to control or regulate the flow of fluids (liquids or gases). Orifices are widely used in various applications to manage flow rates, create pressure drops, or measure flow quantities.

As used herein, the term "longitudinal" refers to something that is oriented or occurring along the length or axis of an object or system.

As used herein, the term "sensor module" refers to a compact, integrated unit that contains one or more sensors along with the necessary circuitry to measure, process, and sometimes transmit data. These modules are designed to detect specific physical properties (such as piston displacement, physiological parameters) and convert them into readable signals, which can be interpreted by a system or device.

As used herein, the term "actuate" refers to causing a mechanism or device to operate or set it into motion.

As used herein, the term "sealing component" refers to a part used to create a tight seal between two surfaces, preventing the leakage of fluids (liquids or gases), dust, or contaminants. Sealing components are essential in maintaining the integrity, safety, and performance of medical devices.

As used herein, the term "pressurization" refers to a process of increasing or maintaining the pressure of a gas or fluid within a confined space, system, or environment.

As used herein, the term "inert gas" refers to a gas that is chemically unreactive or highly stable under normal conditions. These gases do not easily form chemical compounds because their atoms have complete electron shells, making them less likely to participate in chemical reactions. Inert gases are used in medical devices where reactions need to be prevented.

As used herein, the term "osmotic pressure" refers to a pressure exerted by a solvent as it passes through a semipermeable membrane to equalize the concentration of solute on both sides of the membrane. This phenomenon occurs during osmosis, where solvent molecules move from a region of lower solute concentration to a region of higher solute concentration, in order to balance the concentrations on either side of the membrane.

As used herein, the term "semipermeable membrane" refers to a membrane that allows some molecules or ions to pass through while blocking others. The key characteristic of a semipermeable membrane is that it selectively permits the movement of certain substances, usually based on size, charge, or other properties, while preventing the passage of larger or differently charged molecules.

As used herein, the term "provision" refers to mechanism, design, or tool providing or supplying something. The provisions may be holes.

As used herein, the term "microprocessor" refers to a small, integrated electronic component that serves as the central processing unit (CPU) of the device, responsible for managing and controlling its functions. The microprocessor plays a critical role in ensuring that the device operates according to specific medical protocols. It processes data from sensors (e.g., piston displacement, blood pressure, glucose levels, or heart rate), makes decisions based on programmed algorithms, and can activate mechanisms like drug delivery systems, stimulation, or external communication.

As used herein, the term "surface compliance" refers to the ability of a material, structure, or component to deform or adapt to the surface it comes into contact with. In other words, it is a measure of how much a surface or object can bend or yield under external pressure or force, allowing it to conform to irregularities or uneven surfaces.

As used herein, the term "stationary guiding component" refers to a fixed part or structure designed to direct or control the movement of the driving component along a specific path or axis. The stationary guiding component helps to maintain precise movement, alignment, or positioning of the driving component without moving itself.

The term "power source" refers to a component that could provide necessary energy to operate a device. Typically, this is a battery housed within the system's case.

The term "microprocessor" (MCU for microcontroller unit) is a small computer on a single metal-oxide-semiconductor (MOS) integrated circuit (IC) chip. A microprocessor contains one or more CPUs (processor cores) along with memory and programmable input/output peripherals. Program memory in the form of ferroelectric Random Access Memory (RAM), Not OR (NOR) flash or One-Time Programmable Read-Only Memory (OTP ROM) is also often included on chip, as well as a small amount of RAM.

The microprocessors may be designed for embedded applications. The microprocessors may comprise various discrete chips.

The term "microprocessor" may be used interchangeably with terms such as "controller," "processor" or "microcontroller" and like.

The term "physiological parameters" include, but are not limited to, subject body temperature, subject heart rate, subject heart rate variability, subject blood gas levels, subject metabolic rate, subject respiration rate, subject blood analyte levels, subject blood pressure, subject pulse pressure, etc.

The term "Bluetooth Low Energy" (BLE) is a wireless personal area network (WPAN) technology designed and marketed by the Bluetooth Special Interest Group (Bluetooth SIG) aimed at novel applications in the healthcare, fitness, beacons, security, and home entertainment industries. It is independent of Bluetooth BR/EDR and has no compatibility, but Basic Rate/Enhanced Data Rate (BR/EDR) and Low Energy (LE) can coexist. The original specification was developed by Nokia in 2006 under the name Wibree which was integrated into Bluetooth 4.0 in December 2009 as Bluetooth Low Energy. All wireless personal area networks (WPANs) including Recommended Dietary Allowance (rDA), Wireless Universal Serial Bus (USB), Bluetooth or ZigBee come under the scope of the present invention.

The term "sensor" is a device, module, machine, or subsystem whose purpose is to detect events or changes in its environment and send the information to other electronics, frequently a computer processor. A sensor is always used with other electronics.

The term "semipermeable membrane" is a type of biological, synthetic, or polymeric membrane that allows certain molecules or ions to pass through it by diffusion—or occasionally by more specialized processes of facilitated diffusion, passive transport, or active transport. The rate of passage depends on the pressure, concentration, and temperature of the molecules or solutes on either side, as well as the permeability of the membrane to each solute. Depending on the membrane and the solute, permeability may depend on solute size, solubility, properties, or chemistry.

As used herein, the term "active wearable medical device (AWMD)" refers to a compact, portable medical apparatus designed to be worn or affixed on the body of a subject, which automatically or semi-automatically delivers precise doses of therapeutic agents (e.g., drugs, hormones, biologics) to a patient over a prescribed period. It typically includes a drug chamber, a pumping mechanism (active or passive), and one or more delivery interfaces (such as a catheter, microneedles, or infusion set) that enable transdermal, subcutaneous, or intradermal administration of the drug.

As used herein, the term "fluid chamber" refers to an enclosed chamber or a compartment that stores a fluid (e.g., liquid) to support osmosis. The fluid chamber is typically made from biocompatible materials and is fluidically connected to the drug delivery mechanism (e.g., a pump, microfluidic channel, or delivery port). It may be rigid, flexible, or expandable depending on the design of the device.

As used herein, the term "channel" refers to a defined fluidic pathway or conduit. The channel could guide the flow of the drug formulation from one component (e.g., drug chamber or pump) to another (e.g., delivery interface such as a microneedle, catheter, or nozzle) or a body of a mammal. The channel could ensure controlled and directed movement of the drug and may be part of a microfluidic system for precise dosing.

As used herein, the term "fluidically coupled" refers to that two or more components in a system are connected in such a way that a fluid (e.g., liquid drug, gas, or biological fluid) can flow or be transmitted between them, either directly or through intermediate conduits such as tubes, channels, or valves. Fluidically coupled components enable controlled transfer of fluid, such as from a drug chamber to a pump, and from the pump to a delivery interface (e.g., microneedle or catheter).

As used herein, the term "expandable elastomeric bladder" refers to a flexible, stretchable fluid-holding component made from elastomeric (rubber-like) material that can expand to store a fluid (e.g., a liquid drug) and contract to release it. It is used in wearable drug delivery systems to provide a passive or semi-passive pumping mechanism based on the elastic recoil of the material.

As used herein, the term "rigid reservoir" refers to a non-deformable, fixed-volume container used to store a liquid or fluid formulation (e.g., a drug) within a medical or drug delivery device. Unlike flexible or expandable reservoirs, a rigid reservoir does not change shape or volume as fluid is filled or dispensed. The rigid reservoir enables diffusion of the fluid across the semipermeable membrane to dissolve an osmotic agent in the osmotic agent chamber and generate an osmotic gradient to drive the piston.

As used herein, the term "hydrogel reservoir" refers to a storage component in a drug delivery device that contains a hydrogel. The hydrogel acts as both a drug carrier and a release medium, enabling controlled release of the drug over time through diffusion, swelling, or degradation. The hydrogel releases the fluid over time to enable the passive ingress flow of the fluid to the osmotic agent chamber from the hydrogel reservoir.

As used herein, the term "microfluidic reservoir" refers to a small-volume chamber that stores fluid within a microfluidic architecture. It is typically fabricated using precise micro-scale techniques and biocompatible materials.

As used herein, the term "Integrated Flow Restrictor" refers to a built-in microstructure (e.g., a narrow channel, porous membrane, or valve) that resists fluid flow to regulate the delivery rate. This restrictor may be passive (based on geometry or material properties) or active (responding to pressure, temperature, etc.)

As used herein, the term "catheter" refers to a conduit to transport drugs from a reservoir or pump to a targeted internal location such as a vein, artery, organ, or body cavity.

As used herein, the term "Targeted administration" refers to the precise delivery of a drug or therapeutic agent to a specific tissue, organ, cell type, or site within the body, rather than systemic distribution. The goal is to maximize therapeutic effect at the desired site while minimizing side effects elsewhere.

As used herein, the term "active operated chamber" refers to a fluid chamber or compartment within a drug delivery device that dispenses its contents using an external or internal energy source or actuation mechanism, rather than relying solely on passive forces like gravity or elastic recoil.

As used herein, the term "passive operated chamber" refers to a fluid chamber or compartment within a drug delivery device that dispenses its contents without the use of active or powered components, relying instead on inherent physical forces such as gravity, elastic recoil, osmotic pressure, or capillary action to drive fluid flow.

As used herein, the term "biocompatible material" refers to any substance—natural or synthetic—that is compatible with living tissue and does not cause harmful effects (such as toxicity, inflammation, or immune rejection) when in contact with the body or bodily fluids, either temporarily or over extended periods.

As used herein, the term "dissolvable material" refers to substance that is capable of breaking down and going into solution when exposed to a specific solvent—typically water or bodily fluids—within a defined period. The dissolvable materials are used to release therapeutic agents or eliminate the need for removal of the device or its components.

As used herein, the term "plurality of drug chambers" refers to two or more separate compartments or chambers within a drug delivery device, each capable of storing and/or delivering a drug formulation. These chambers may contain the same drug for redundancy or extended dosing, or different drugs for combination therapies or sequential administration.

As used herein, the term "sequential discharge" refers to the controlled, stepwise release of fluids or drug formulations from two or more drug chambers, reservoirs, or delivery elements in a predetermined order over time. It is commonly used to achieve multi-phase therapy, timed release, or layered dosing.

As used herein, the term "combination of discharge" refers to the coordinated release of fluids or drug formulations from multiple chambers or sources, wherein the discharges may occur simultaneously, sequentially, intermittently, or in overlapping patterns, depending on therapeutic requirements or device programming.

As used herein, the term "real-time imaging and navigation guidance device" refers to a medical system or tool that captures, processes, and displays visual data continuously or near-instantaneously to assist clinicians or robots in locating, targeting, and guiding instruments or therapies within the body during diagnostic or interventional procedures.

As used herein, the term "attachment component" refers to a structural or functional element of a device that enables it to be secured, mounted, or affixed to another object or surface—such as a user's body, clothing, or another medical device.

Embodiments of the invention are applicable to humans and more generally to mammals (host). Present disclosure provides a device for controlled delivery of drugs. "Drug" in context of the present disclosure may include any therapeutic active agent and/or a biologically active agent (i.e., an active ingredient in a pharmaceutical composition that is biologically active, such as a vaccine). "Drug" in context of the present disclosure is not limited by molecular weight of such agents. Terms "drug," "active agent," "therapeutic agent," "beneficial agent," or "pharmaceutical fluid" are used interchangeably. Drug as used herein refers to a single drug or multiple types of drugs. In some embodiments, the drug is one of an injectable drug such as without limitation Adalimumab, dulaglutide, enosumab, ustekinumab, pneumococcal 13-valent vaccine, romiplostim, paliperidone palmitate, erenumab, benralizumab, ixekizumab, ofatumumab, pegfilgrastim, guselkumab, golimumab, asfotase alfa, and blinatumomab. In some embodiments, the drug is a repurposed drug such as without limitation apixaban, lenalidomide, semaglutide, rivaroxaban, dapagliflozin, pomalidomide, fingolimod, ozanimod, tofacitinib, ambrisentan, axitinib, lenvatinib, and cariprazine.

Embodiments relate to an active implantable medical device (AIMD). The AIMD comprises a drug chamber, a motor chamber, a piston, and an electronic module. The drug chamber comprises a drug. The motor chamber comprises a housing, a motor, and a driving component. The motor may be a stepper motor. The driving component is coupled to the motor via a motor shaft such that when the motor is operated the driving component also rotates. The driving component may be a helical threaded screw which converts the rotational motion to a linear motion. The piston is affixed to a first end of the driving component. The first end is an end which is towards one or more orifices through which the drug is discharged from the AIMD to outside the AIMD (i.e., a subject). As the piston is affixed to the first end of the driving component, the piston moves longitudinally towards the one or more orifices, which discharges the drug from the drug chamber to the subject (i.e., outside the AIMD). The subject may be a living being (e.g., a human, animal, a mammal, etc.).

The active implantable medical device (AIMD) may comprise a sensor module and an electronic module. The sensor module is configured to measure displacement of a piston. The electronic module communicates a signal to the stepper motor to control the stepper motor and regulate the one-way flow of the drug based on the displacement of the piston. Additionally, the electronic module comprises a power supply module for supplying energy to the electronics module, the sensor module, and the motor. The device is designed with a tubular structure for subcutaneous implantation. The AIMD continuously releases the drug at prescribed times, while the sensor module monitors relevant parameters, for example, displacement. A communication web connects all modules, ensuring the synchronized movement of the piston towards the drug chamber with each release, with the motor actuating this action and the sensor detecting the piston's movement.

In an embodiment, the dose-to-dose variation of a drug via the device is ±25% or less by volume. In an embodiment, the dose-to-dose variation or flow discharge accuracy (used interchangeably throughout the specification) of a drug via the device is ±20% or less by volume. In an embodiment, the device has a dose accuracy of no wider than ±15% of the intended target dose.

In another embodiment, the flow discharge accuracy is ±10%. In another embodiment, the flow discharge accuracy is ±5%. In another embodiment, the flow discharge accuracy is ±3%.

In some embodiments, the AIMD has different modules such as without limitation a drug chamber, a motor chamber, a power module, a valve module, a sensor module, and an electronic module. These modules are interconnected with each other. A person skilled in the art would understand that different ways of interconnecting these modules is possible, such as but not limited to screwing them together, creating notches at the ends of the modules, etc. In some embodiments, each module is threaded with male-female threads such that the first module screws into the second module, the second module screws into the third module, and the third module screws into the fourth module.

In some embodiments, the sensor module and the electronic module could be adhesively bonded to the device tube.

In an embodiment, the AIMD has a tubular structure having an outermost casing. In an embodiment, the casing is made up of a biocompatible material or Food and Drug Administration (FDA) approved material, such as without limitation Titanium. In an embodiment, the casing has housing to connect different modules. As per principle of operation of the implantable, a person skilled in the art would understand that different ways of putting electrical circuits in the casing is possible, such as but not limited to gluing or imprinting. In some embodiments, the housing material provides durability, corrosion resistance, and compatibility with body and with the fluids within the device, such as but not limited to Titanium.

In an embodiment, the device tube has an outer diameter between 3 mm to 5 mm, such as 3 mm, 3.5 mm, 4 mm, 4.5 mm, etc. In an embodiment, the casing has a wall thickness about 0.25 mm, 0.3 mm, 0.4 mm, 0.5 mm, 0.6 mm, 0.7 mm, 0.8 mm, 0.1 mm.

In another aspect, an active implantable medical device (AIMD) is described. The AIMD comprises a drug chamber, a motor chamber, a stationary guiding component, and an electronic module. The drug chamber comprises a drug. The motor chamber comprises a housing, a motor, and a driving component. The stationary guiding component comprises a provision through which the driving component protrudes longitudinally. The electronic module actuates the motor to operate the driving component and protrude longitudinally through the stationary guiding component to discharge the drug outside the AIMD through one or more orifices. The driving component may comprise a flattened surface at a first end to push the drug through the one or more orifices. The AIMD may comprise a sealing component between the stationary guiding component and the driving component. The driving component is operable to function as a piston to discharge the drug outside the AIMD through one or more orifices. The driving component may comprise a helical threaded screw. The other embodiments and variations described in this disclosure are applicable to this aspect as well.

Technical Problem: The convention implantable devices lack efficient and controlled delivery of drugs to a subject, such as a human or animal. The challenge lies in ensuring that the drug is discharged from the drug chamber in a precise and reliable manner. A key issue is the need for a mechanism to move the piston, which discharges the drug, in a controlled way. This requires converting the rotational motion of the motor into the linear motion needed to move the piston longitudinally towards the orifices, thereby releasing the drug.

Technical Solution to Problem: The technical solution describes the controlled and precise delivery of a drug from an active implantable medical device (AIMD) to a subject (such as a human or animal). This is achieved through a mechanism that converts rotational motion from a stepper motor into linear motion to move a piston in the drug chamber. The solution involves using a helical threaded screw as the driving component, which rotates when the motor is operated. This rotational motion is converted into linear motion, causing the piston to move longitudinally towards the orifices of the device, thereby discharging the drug from the chamber to the outside (i.e., to the subject). The system ensures accurate and controlled drug delivery by precisely moving the piston and allowing for the regulated release of the drug, addressing the need for effective, reliable drug administration in an implantable medical device.

Advantageous effects of invention: The system offers several advantageous effects, including precise and controlled drug delivery, which ensures accurate dosing and reliable release of medication from the drug chamber to the subject. The use of a stepper motor and a helical threaded screw enables precise control over the piston's movement, minimizing the risk of over or under-dosing. This design reduces the need for manual intervention, making the drug administration process more automated and convenient for patients, which in turn enhances patient compliance. The compact and efficient mechanism is ideal for implantable medical devices, ensuring long-term, reliable operation within the body. By minimizing human error and allowing for regulated drug release, the system provides consistent and continuous medication delivery, which is crucial for chronic conditions. Additionally, the device's versatility makes it suitable for a variety of subjects, including humans and animals. Overall, this technology offers a more reliable, convenient, and personalized approach to drug delivery, potentially improving treatment outcomes while reducing healthcare burdens.

DESCRIPTION OF EMBODIMENTS

FIG. 1 illustrates an active implantable medical device (AIMD) comprising a lead screw and a motor for actuating a piston in longitudinal direction, according to one or more embodiments. The AIMD comprises a drug chamber 102, a motor chamber 106, a piston 114 and an electronic module 116. The drug chamber 102 comprises a drug 104. The motor chamber 106 comprises a housing 108, a motor 110, and a driving component 112. The motor 110 may be a stepper motor or a DC motor. The driving component 112 is coupled to the motor 110 via a motor shaft. The driving components comprise threads that are placed externally onto the body of the driving component 112. The driving component 112 itself may be a helical threaded screw. The motor shaft comprises internal threads. The internal threads of the motor shaft match the threads of the driving component 112 such that when the motor 110 is operated the driving component 112 also rotates. The piston 114 is affixed to the first end of the driving component 112. The motor shaft functions as the guiding component enabling the piston 114 and the driving component 112 to operate together and move longitudinally.

The piston 114 and the driving component 112 move together longitudinally to discharge the drug 104 upon actuating the motor 110. The driving component 112 may rotate and protrude through the motor 110. The driving component 112 may be a helical threaded screw which converts the rotational motion to a linear motion. The driving component 112 comprises a length that is equal to sum of (a) a length of the motor, (b) a length between an initial position of the first end of the driving component and a motor position, and (c) a length between the initial position of the first end of the driving component and a displacement position of the first end of the driving component 112.

The piston 114 is affixed to a first end of the driving component 112. The first end is an end which is towards one or more orifices 118 through which the drug is discharged from the AIMD to outside the AIMD (i.e., a subject). As the piston 114 is affixed to the first end of the driving component 112, the piston 114 and the driving component 112 move together longitudinally towards the one or more orifices 118, which discharges the drug 104 from the drug chamber 102 to the subject (i.e., outside the AIMD). The subject may be a living being (e.g., a human, animal, a mammal, etc.). The outer circumference of the piston 114 comprises a sealing component. The outer circumference of the piston 114 is in surface compliance with the AIMD. The sealing component prevents leakage of the drug from the drug chamber 102 to the motor chamber 106. The sealing component prevents contamination of the drug 104 in the drug chamber 102 with a fluid or gas in the motor chamber 106.

In an embodiment, the piston 114 may be located either inside or outside the drug chamber 102. If the piston 114 is located outside the drug chamber 102, the drug chamber 102 may be collapsible. The collapsibility may be achieved by constructing the drug chamber 102 with materials that enable such deformation. In an embodiment, the AIMD may be drug-filled or may be configured to receive a prefilled drug chamber that is inserted or connected into the device.

The active implantable medical device may comprise a sensor module 117. The sensor module 117 is configured to measure displacement of the piston 114. The electronic module 116 communicates a signal to the motor 110 to control the motor 110 and regulate the one-way flow of the drug 104 based on the displacement of the piston 114. Additionally, the electronic module 116 comprises a power supply module for supplying energy to the electronics module 116, the sensor module 117, and the motor 110. The device is designed with a tubular structure for subcutaneous implantation. The device continuously releases the drug 104 at prescribed times, while the sensor module 117 monitors relevant parameters, for example, displacement. A communication web connects all modules, ensuring the synchronized movement of the piston towards the drug chamber 102 with each release, with motor 110 actuating this action and the sensor module 117 detecting the movement of the piston 114.

The electronic module 116 may be in a hollow shape or conical shape. The hollow shape or conical shape is adapted to enable the protrusion of the driving component 112 through the electronic module 116 at the back of the motor 110. The conical shape is adapted to achieve a compact sized AIMD. The electronic components may be placed around the path of the driving component 112 at the back of the motor 110.

The AIMD may receive interstitial fluid through a channel from one of a fluid storage or from outside the AIMD. The fluid storage may be within the AIMD or outside the AIMD. The interstitial fluid may enter and occupy the space created due to the displacement of the piston 114. The ingress flow or entry of the interstitial fluid restricts the creation of the vacuum in the displacement area of the piston 114. The AIMD may comprise one or more mechanisms (described below in FIG. 6, FIG. 7, and FIG. 8) to allow entry of the interstitial fluid and to restrict creation of vacuum within the AIMD.

In some embodiments, the electronic module 116 comprises chips, electronics housing, and/or electronic components. In some embodiments, the electronic module 116 comprises without limitation one or more of sensors, data storage, communication system, power switch to ensure proper functioning. Sensors continuously or discontinuously monitor various parameters such as drug levels within a patient body and/or within the device, patient vitals, and environmental conditions, etc., to provide real-time data to the microprocessor for processing. The controllers could manage operations such as receiving data from various device components such as sensors and/or battery. The actuator of the controller and the valve module work together to release medication as needed. The communications system, featuring a Bluetooth module, facilitates wireless communication with external devices for data exchange and remote control. Wi-Fi enables internet connectivity for remote monitoring and updates, while inductive and magnetic pulses support wireless charging and communication through the battery charge coil or pump coil. Light sensors detect and communicate using light pulses, and the system also utilizes other known communication methods. In an embodiment, the electronic module may also form a connection with a handheld device that could be used by a user (e.g., patient, caretaker, etc.) to monitor and control the device remotely.

Data logging and storage functionalities ensure that the AIMD logs and retains valuable information such as dosing history, sensor readings, fault conditions, and battery status, which are crucial for monitoring and adjusting treatment. Additional outputs such as electromagnetic fields are used for therapeutic purposes, while light pulses are emitted for communication or therapy.

In an embodiment, the power switch controls the device's power state, allowing it to be turned on or off as needed. In an embodiment, a processor or simple timer manages the device's operations, including recording and adjusting medication dosing based on sensor inputs, monitoring fault conditions, processing sensor data for accurate operation, and overseeing battery status and power usage. In an embodiment, it may also store relevant patient medical history for reference. The system ensures that the AIMD device operates efficiently and effectively, providing necessary treatment while maintaining patient safety.

In some embodiments, the microprocessor (or processor) is configured to analyze the medical characteristics of the patient to determine a symptom associated with a medical condition such as without limitation an opiod overdose, measuring physiological parameters of the user (e.g., patient) of the device. In an embodiment, the microprocessor is configured to analyze medical characteristics of the patient to determine a symptom associated within the patient, wherein the symptom corresponds to a decrease in respiratory rate, a decrease in heart rate, a decrease in blood pressure, deviations from normal body temperature, passing out or an unresponsive loss of consciousness, skin color changes, abnormal breathing, fast, slow or irregular breathing, severe chest pain, seizures, severe headaches, difficulty in breathing, delirium, agitation, and/or anxiety. In some embodiments, the microprocessor is further configured to send an alert or notification wirelessly upon detection of the symptom.

The wireless communication system of the electronic module 116 enables the device to transmit data to external devices, allowing for remote monitoring and adjustments. The microprocessor plays a central role in managing data flow and device control, processing inputs from the sensors and executing commands to the actuator.

In some embodiments, the sensor module 117 monitors one or more physiological parameters of a subject. The sensor module 117 communicates a signal to the electronic module when the one or more physiological parameters of the subject is abnormal. The electronic module 116 actuates the motor in response to a signal received from the sensor module 117. The AIMD further comprises a biosensor coupled to the microcontroller to verify medical characteristics of the patient prior to delivery of a drug. The biosensors provide real-time data of drug levels and/or health related markers, offering valuable insights for personalized treatment for triggering by either the skin touch or the integrated sensor device. For example, a biosensor can monitor an opioid, the opioid agonist, or the partial opioid agonist, wherein the biosensor comprises a pulse oximeter, a heart rate sensor, an Electrocardiogram (ECG) sensor, a skin sensor, a temperature sensor, and/or a blood flow sensor.

The microprocessor in the AIMD handles data flow by acting as the central processing unit that coordinates all the AIMD functions. It receives input from various sensors, which monitor the internal environment and drug levels. The microprocessor processes this data to determine the appropriate actions, such as adjusting the dosage or triggering the actuator to release medication. It also manages communication with external devices through wireless modules, ensuring that data such as dosing history, sensor readings, and battery status are transmitted for remote monitoring and control. Additionally, the microprocessor stores critical data in its memory, including fault conditions and medical history, which can be accessed and analyzed to optimize treatment. By efficiently managing data flow, the microprocessor ensures that the device operates smoothly, making real-time adjustments based on sensor inputs and maintaining reliable communication with external systems. This integrated approach helps maintain the device's performance and enhances patient safety.

In an embodiment, the AIMD has a power supply module. The electronic module and the power supply module are separated from the rest of the modules of the device by a waterproofing. A power module of an implantable drug delivery device comprises at least one power source and a power switch. In some embodiments, the device harnesses energy (or power) from the environment through energy harvesting. The energy could be harvested by converting kinetic energy of body movements into electrical power, or by utilizing body heat to generate power, or by capturing energy from the heartbeat, or by using the body's electromagnetic fields. In some embodiments, the device receives power through induction charging from an external source. In some embodiments, the power switch is a magnetic field activated switch. The power switch can also utilize other mechanisms available in the environment to turn the power on permanently. The power source and the power switch work together to ensure the device operates reliably, utilizing available energy efficiently and maintaining a consistent power supply. The device relies on a wireless charger to recharge its rechargeable battery, ensuring a consistent supply of electric power.

In an embodiment, the AIMD may be of various shapes including but not limited to tubular, circular, or oval configurations, which are common in AIMDs.

Figure 2A:
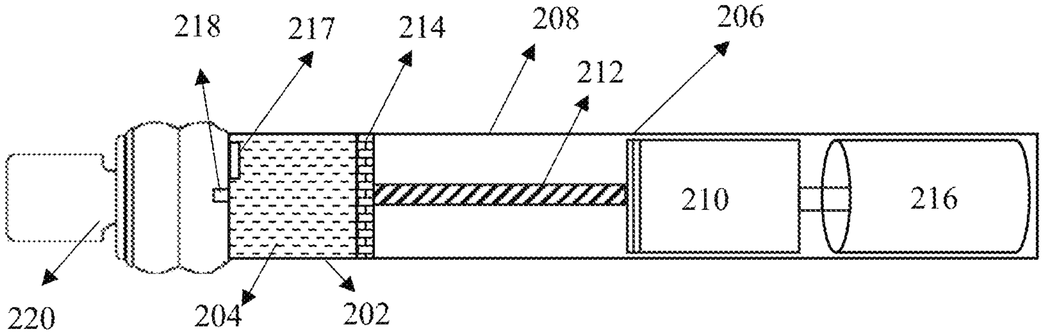
FIG. 2A illustrates an AIMD comprising a check valve, according to one or more embodiments.

FIG. 2A illustrates an AIMD comprising a check valve 220, according to one or more embodiments. The other components (such as drug chamber 202, drug 204, motor chamber 206, housing 208, motor 210, driving component 212, piston 214, electronic module 216, sensor module 217, one or more orifices 218), and the workings of the AIMD are already explained in FIG. 1. The AIMD may comprise a check valve 220 as shown in FIG. 2A. The check valve 220 is also known as a non-return valve. The check valve 220 is coupled to the drug delivery end of the AIMD. The check valve 220 is more specifically coupled to the AIMD via the one or more orifices 218. The check valve 220 is adapted to allow the fluid (liquid or gas) to flow in one direction while preventing reverse flow. The check valve 220 allows one-way flow of the drug from the drug chamber 202 to outside the AIMD through the one or more orifices 218. The check valve 220 blocks entry of a fluid to the drug chamber from outside the AIMD. The check valve 220 operates automatically, using a movable component like a disc, ball, or flap that opens under forward flow pressure and closes when flow reverses. This prevents backflow, protects equipment, contamination, and maintains system pressure. The check valve 220 remains closed until the incoming pressure when the drug releases reaches a threshold pressure.

Figure 2B:
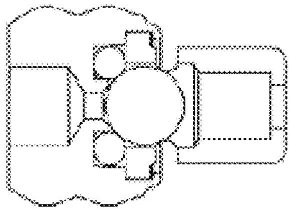
FIG. 2B depicts a schematic diagram of the check valve shown in FIG. 2A.

The check valve 220 shown in FIG. 2A is a spring-loaded ball check valve. The spring-loaded ball check valve is a variation of the ball check valve. In this type of valve, a spring is added to the design to ensure quicker and more reliable sealing when the flow reverses. The primary components include a spherical ball, a spring, a seat for sealing, and a housing to contain the mechanism. The working principle involves two key stages. During forward flow, fluid pressure overcomes the spring's force and pushes the ball away from its seat, allowing fluid to flow through the spring-loaded ball check valve. The spring compresses as the ball moves, creating a clear pathway for the fluid. When the flow stops or reverses, the spring forces the ball back onto the seat, providing a tight seal that prevents backflow. This design ensures faster closure compared to standard ball check valves, making it ideal for systems prone to water hammer or sudden pressure changes. FIG. 2B depicts a schematic diagram of the check valve shown in FIG. 2A.

Figure 3A:
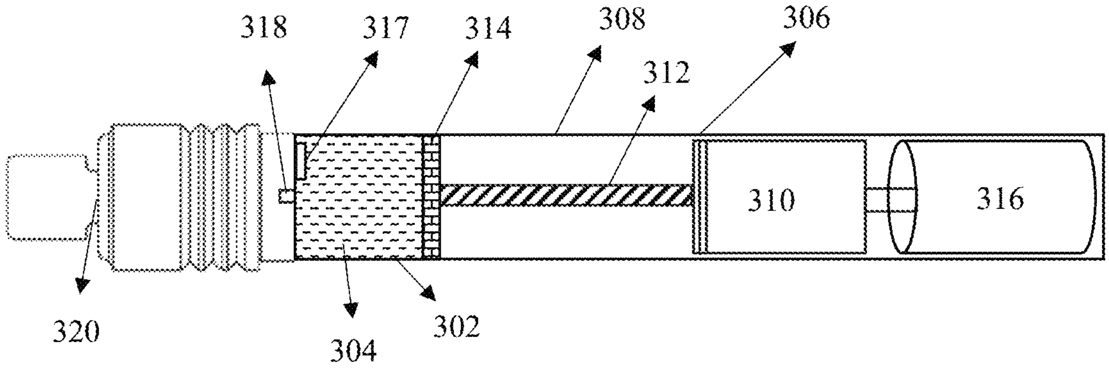
FIG. 3A illustrates an AIMD comprising a check valve, according to one or more embodiments.

Similarly, FIG. 3A illustrates an AIMD comprising a check valve 320, according to one or more embodiments. The other components (such as drug chamber 302, drug 304, motor chamber 306, housing 308, motor 310, driving component 312, piston 314, electronic module 316, sensor module 317, one or more orifices 318) and the workings of the AIMD are already explained in FIG. 1. The check valve 320 shown in FIG. 3A is a ball check valve. The ball check valve is a type of check valve that uses a spherical ball to control the flow of fluid, allowing it to pass in one direction while preventing reverse flow. During forward flow, the fluid pressure pushes the ball away from its seat, creating a pathway for the fluid to pass. When reverse flow occurs, the pressure forces the ball back onto its seat, creating a tight seal that blocks the flow. The check valve 320 operates automatically based on pressure differences and does not require external controls, though some designs incorporate a spring to ensure quicker closure and prevent issues like water hammer. The check valve 320 remains closed until the incoming pressure reaches a threshold pressure.

Figure 3B:
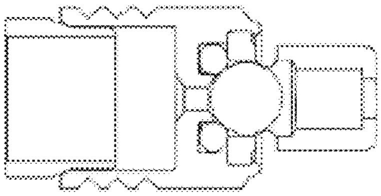
FIG. 3B depicts a schematic diagram of the check valve shown in FIG. 3A.

The ball check valves are valued for their simple, compact design and minimal maintenance. FIG. 3B depicts a schematic diagram of the check valve shown in FIG. 3A.

Figure 4:
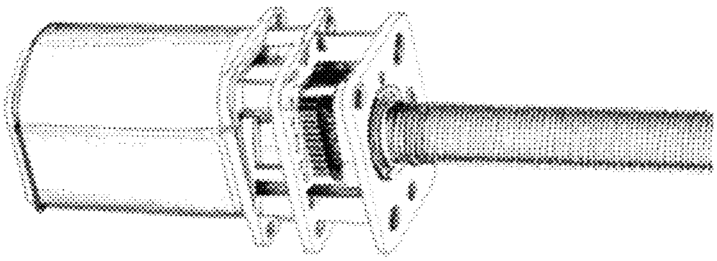
FIG. 4 illustrates a lead screw and motor arrangement, according to one or more embodiments.

FIG. 4 illustrates a lead screw and motor arrangement, according to one or more embodiments. The lead screw is affixed to the motor shaft such that when the motor shaft rotates, the lead screw rotates. The lead screw may be affixed to the motor shaft through a gear mechanism. The gear mechanism may be compact to achieve compact size. The lead screw is a mechanical screw with helical threads. The helical threads may be located on the outer surface of the screw. The lead screw and motor arrangement may comprise a piston (not shown in FIG. 4). The piston comprises a hole in the centre. The piston also comprises threads on the inner surface of the hole in the piston. The threads in the piston match with the threads in the lead screw such that when the motor shaft rotates, the piston moves forward like the tool holder in a lathe. The movement of the piston pushes the drug (e.g., medication) through the valve.

Figure 5A:
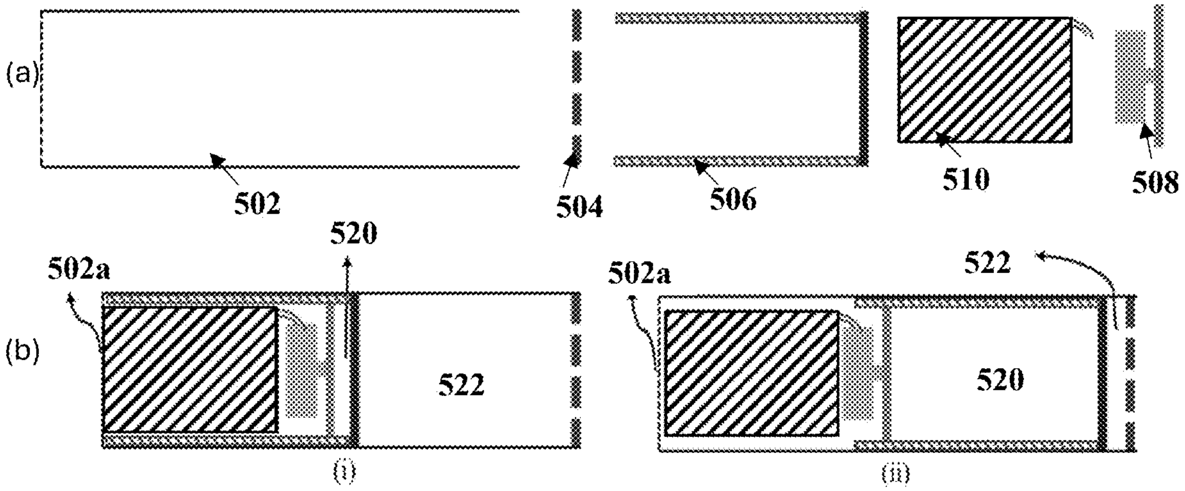
FIG. 5A illustrates an AIMD comprising a moving grooved cylinder on lead screw, according to one or more embodiments.

FIG. 5A illustrates an AIMD comprising a moving grooved cylinder on lead screw, according to one or more embodiments. Referring to FIG. 5A, the external enclosure 502 is the main outer cylinder that has a first open end and a second perforated end 502*a*. The open end can accommodate the valve 504. The piston assembly 506 comprises a piston fixed to a separate cylinder that has an internal groove, similar to the thread of a nut. The motor and shaft assembly 508 comprises a motor that has a shaft end that has an outer groove, similar to the thread of a bolt or screw. When the motor shaft rotates, the grooved shaft interacts with the grooved cylinder that the piston is fixed to. This causes the piston assembly 506 to move forward and backward, similar to a lead screw mechanism. In some embodiments, the motor shaft is not able to move laterally. Instead, the rotating motion of the motor shaft pushes the cylinder that the piston is fixed to. This causes the piston to move forward. The movement of the piston pushes the medication 522 through the valve 504 at the front. The space created on the motor side of the piston is filled with interstitial fluid 520 coming through the perforated holes in the side wall of the external enclosure 502. The interstitial fluid 520 filling the space behind the piston helps maintain the pressure and prevent a vacuum from forming, which could otherwise cause the system to collapse. The electronics unit 510 comprises a power source comprising a battery and electronic components.

In some embodiments, the battery and electronic components are housed separately, likely in a smaller inner cylinder. This allows the main piston assembly to move without the need to accommodate the electronics within the same space.

An embodiment relates to a device comprising an external enclosure, a valve, a piston assembly, a motor and shaft assembly, an electronics unit, and a control switch.

Figure 5B:
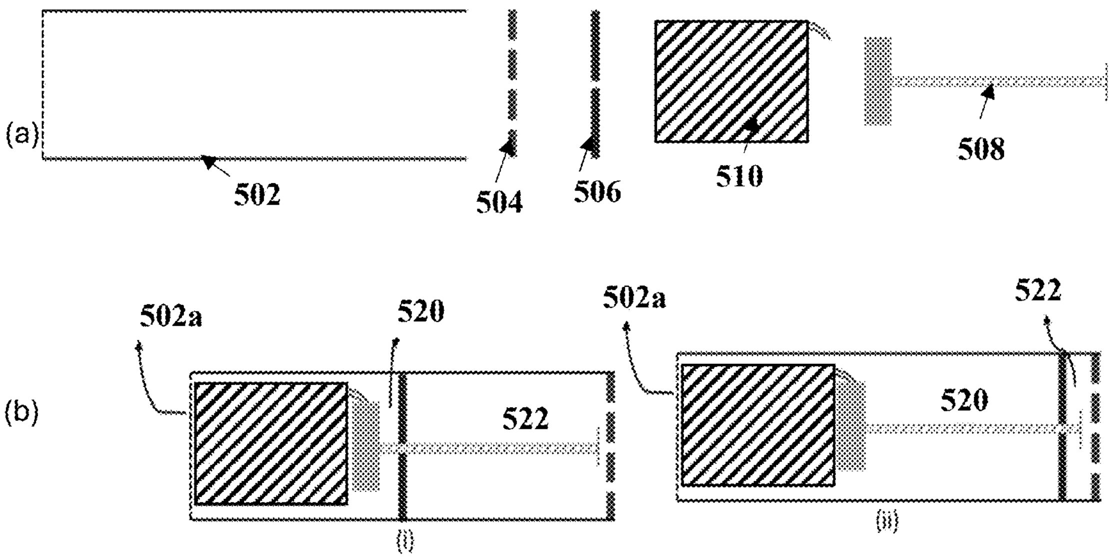
FIG. 5B illustrates an AIMD comprising a moving piston on lead screw, according to one or more embodiments.

FIG. 5B illustrates an AIMD comprising a moving piston on lead screw, according to one or more embodiments. Referring to FIG. 5B, the external enclosure 502 is the main outer cylinder that has a first open end and a second perforated end 502*a*. The open end can accommodate the valve 504. The piston assembly 506 comprises a piston with a hole fixed to a separate cylinder that has internal grooves, similar to the threads of a nut. The motor and shaft assembly 508 comprises a motor shaft. Whether it is a stepper motor or a Direct Current (DC) motor, it functions similar to a lead screw in a lathe, facilitating precise linear movement. The shaft passes through the hole in the piston. As the motor shaft rotates, it moves the piston. This motion mimics the forward movement of a tool holder in a lathe, effectively pushing the piston forward. As the piston advances, it expels medication 522 through the valve 504. Simultaneously, the space created on the motor side of the piston is replenished by interstitial fluid 520 that enters through holes in the side wall of the external enclosure 502, ensuring a continuous operation. The electronics unit 510 comprises a power source comprising a battery and electronic components.

An embodiment relates to a device comprising an external enclosure, a valve, a piston assembly, a motor, and shaft assembly comprising a gear, an electronics unit, and a control switch.

Figure 5C:
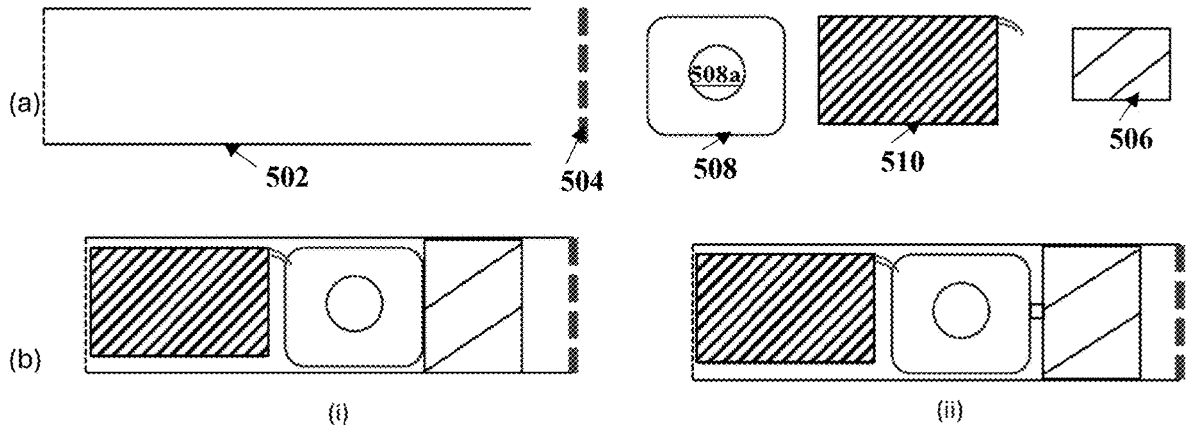
FIG. 5C illustrates an AIMD comprising a moving cylinder using gears, according to one or more embodiments.

FIG. 5C illustrates an AIMD comprising a moving cylinder using gears, according to one or more embodiments. Referring to FIG. 5C, the external enclosure 502 comprises a main outer cylinder with a first open end and a second perforated end, where the open end accommodates the valve. The valve 504 is positioned at the open end of the external enclosure. The piston assembly 506 includes a piston with a hole, fixed to a separate cylinder with internal grooves similar to nut threads. The motor and shaft assembly 508 features a motor shaft, either a stepper or DC motor, functioning like a lead screw in a lathe to facilitate precise linear movement. A gear 508*a* is attached to the motor shaft. The electronics unit 510 controls the motor and the overall device operation. The operation involves a gear mechanism where the gear attached to the motor shaft drives the motor shaft. As the gear rotates, it drives the motor shaft, which passes through the hole in the piston, mimicking the forward movement of a tool holder in a lathe and pushing the piston forward. This movement expels medication through the valve 504. The space created on the motor side of the piston is replenished by interstitial fluid 520 entering through holes in the side wall of the external enclosure 502, ensuring continuous operation. This design simplifies the device using a gear to drive the motor shaft, which in turn moves the piston, ensuring precise and continuous medication delivery.

An embodiment relates to a device comprising an external enclosure, a valve, a submersible pump, an electronics unit, and a control switch. The submersible pump sucks in the fluid and pushes it out.

Figure 5D:
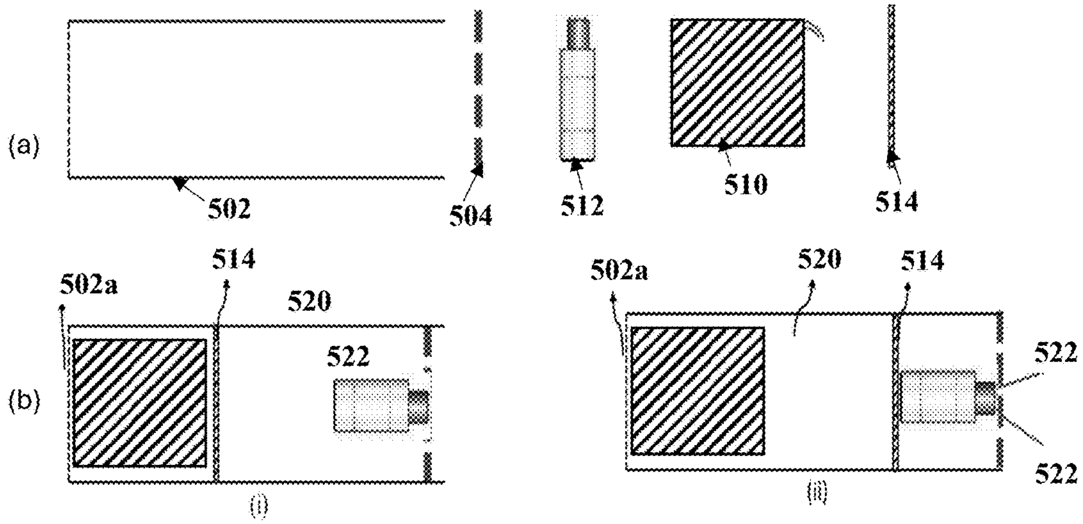
FIG. 5D illustrates an AIMD comprising a submersible pump, according to one or more embodiments.

FIG. 5D illustrates an AIMD comprising a submersible pump, according to one or more embodiments. Referring to FIG. 5D, the external enclosure 502 of the device is designed as a main outer cylinder with a first open end and a second perforated end 502*a*. At the open end, a valve 504 is strategically positioned to facilitate the expulsion of medication D. Inside the enclosure, a submersible pump assembly 512 is placed near the perforated end, where the pump is responsible for sucking in the medication 522 and pushing it out. This submersible pump assembly 512 comprises either a stepper motor or a DC motor, which ensures precise medication 522 movement and effective operation. An integrated electronics unit 510 manages the motor and overall device functionality, allowing for accurate control of the pump's operation. During the pump's mechanism, the motor drives the submersible pump to draw medication 522 in through the perforated end, subsequently pushing it toward the valve 504 at the open end. As the pump operates, the medication is expelled through the valve 504, delivering the necessary medication 522. To maintain continuous operation, any space created by the expelled fluid is replenished by interstitial fluid 520 entering through the perforated end. A sliding spacer 514 maintains a barrier between the drug and the interstitial fluid.

This design not only simplifies the system by eliminating the need for complex piston and gear mechanisms but also enhances fluid handling efficiency, ensuring smooth and reliable medication 522 delivery. The compact nature of the submersible pump assembly 512 further makes this device suitable for a range of medical applications, requiring efficiency and reliability in delivering precise medication. A sliding spacer 514 maintains a barrier between the interstitial fluid and the drug reservoir.

An embodiment relates to a device comprising an external enclosure, a compressible drug chamber, a valve, a submersible pump, electronics unit, and a control switch. The submersible pump sucks in the fluid and pushes it out.

Figure 5E:
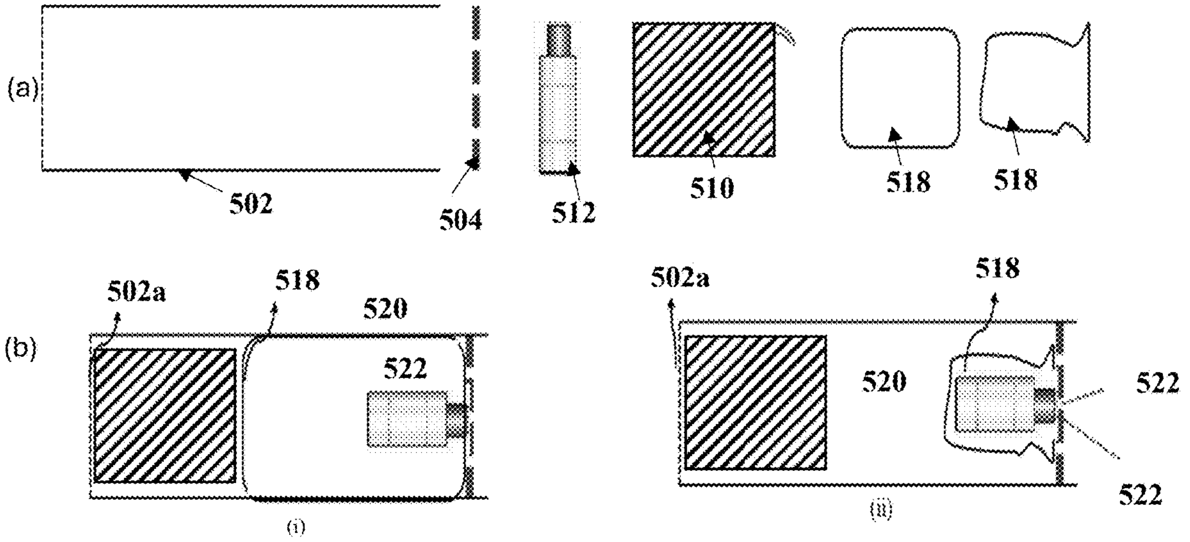
FIG. 5E illustrates an AIMD comprising a submersible pump and a compressible drug chamber, according to one or more embodiments.

FIG. 5E illustrates an AIMD comprising a submersible pump and a compressible drug chamber, according to one or more embodiments. Referring to FIG. 5E, the external enclosure 502 of the device is designed as a main outer cylinder with a first open end and a second perforated end 502*a*. At the open end, a valve 504 is strategically positioned to facilitate the expulsion of medication. Inside the enclosure, a submersible pump assembly 512 is placed near the perforated end, where the pump is responsible for sucking in medication 522 and pushing it out. The submersible pump assembly 512 is driven by either a stepper motor or a DC motor, which ensures precise drug movement and effective operation. An integrated electronics unit 510 manages the motor and overall device functionality, allowing for accurate control of the pump's operation. During the pump's mechanism, the motor drives the submersible pump assembly 512 to draw medication 522 in through the perforated end, subsequently pushing it toward the valve 504 at the open end. As the submersible pump assembly 512 operates, the drug is expelled through the valve 504, delivering the necessary medication. To maintain continuous operation, any space created by the expelled fluid is replenished by interstitial fluid 520 entering through the perforated end. Due to the pressure exerted by the interstitial fluid and removal of the drug from the compressible drug chamber 518 compresses gradually.

This design not only simplifies the system by eliminating the need for complex piston and gear mechanisms but also enhances drug dosing efficiency, ensuring smooth and reliable medication delivery. The compact nature of the submersible pump further makes this device suitable for a range of medical applications, requiring efficiency and reliability in delivering precise medication.

Figure 6A:
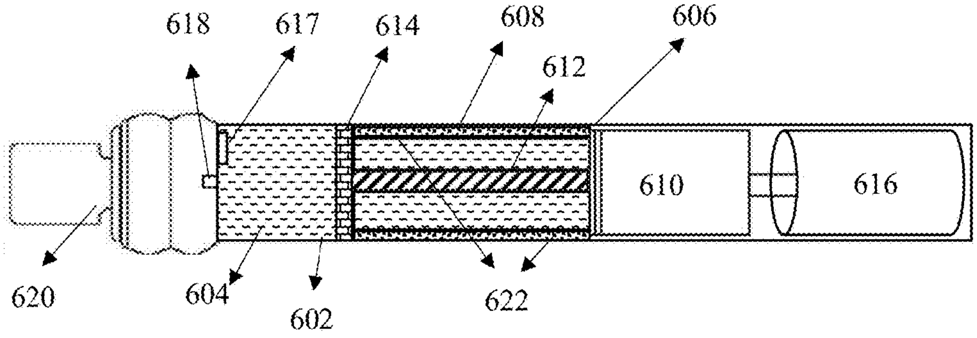
FIG. 6A illustrates an AIMD comprising a semipermeable membrane on a motor chamber, according to one or more embodiments.

FIG. 6A illustrates an AIMD comprising a permeability module 622 on a motor chamber 606, according to one or more embodiments. The AIMD in FIG. 6A is similar to the one shown in FIG. 1. The other components (such as drug chamber 602, drug 604, motor chamber 606, housing 608, motor 610, driving component 612, piston 614, electronic module 616, sensor module 617, one or more orifices 618, check valve 620) of the AIMD are already explained in FIG. 1. The AIMD shown in FIG. 6A comprises the permeability module 622 on the housing (outer surface) of the motor chamber 606 in addition to the AIMD shown in FIG. 1. The housing of the motor chamber 606 comprises the permeability module 622. The permeability module 622 functions to seal the interior of the AIMD from the external environment, allowing only specific fluid molecules to permeate through a membrane plug into the device's interior. In an embodiment, permeability module 622 also effectively prevents items within the AIMD, such as an osmotic agent and a drug 604, from passing through it.

In an embodiment, the first end of the permeability module 622 has a semipermeable membrane (or membrane plug) supported by a plate, and the other end of the permeability module 622 has holes to allow inflow of fluid inside the device. In an embodiment, the permeability module 622 may have a hollow fiber or bundles of hollow fibers arranged together, forming a bridge for entry of outside fluid into the device. In an embodiment, permeability module 622 may also be designed to separate solutes from a feed solution, such as blood serum, using a semipermeable membrane.

Figure 6B:
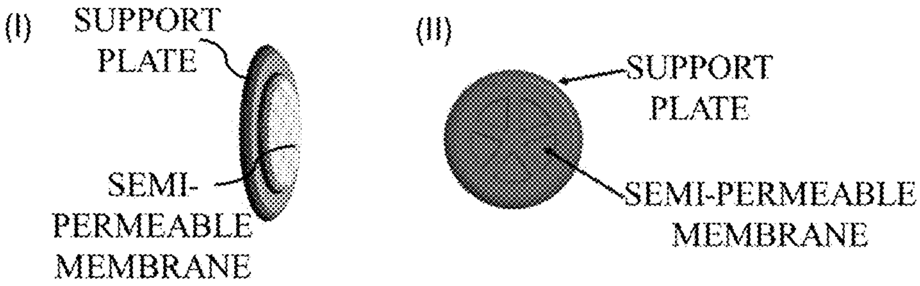
FIG. 6B illustrates a schematic of a flat membrane as a permeability module, according to one or more embodiments.

In an embodiment, permeability module 622 has a permeability membrane held by a support structure as shown in FIG. 6B. In an embodiment, support structure or plate could be made of a biocompatible material and/or metal such as without limitation titanium, Food and Drug Administration (FDA) approved material such as stainless steel. In some embodiments, the semipermeable membrane is supported by one plate or sandwiched between two rigid plates. These plates have a plurality of holes in front and back of the semipermeable membrane. The arrangement of these holes determines the flow rate of fluid passing through them. (Liquid or fluid are interchangeably used throughout the description.)

In an embodiment, a fluid ingress flow can be adjusted by adjusting the alignment of the rigid discs. When the rigid discs are aligned differently, the flow rate changes. When the rigid discs are aligned such that none of the holes from the first plate overlay the holes in the second plate, the flow rate through the sandwich structure is nearly zero. Conversely, when the rigid discs are aligned such that all the holes in the first plate overlay the holes in the second plate, the flow rate through the sandwich structure is maximum. By aligning the rigid discs so that partial areas of the holes in the first plate overlay the holes in the second plate, the flow rate falls between nearly zero and the maximum. This intermediate configuration allows fine-tuning of the ingress flow rate. In some embodiments, ingress flow rate of fluids through the permeability module could be adjusted by changing the membrane's permeability or its thickness.

Figure 6C:
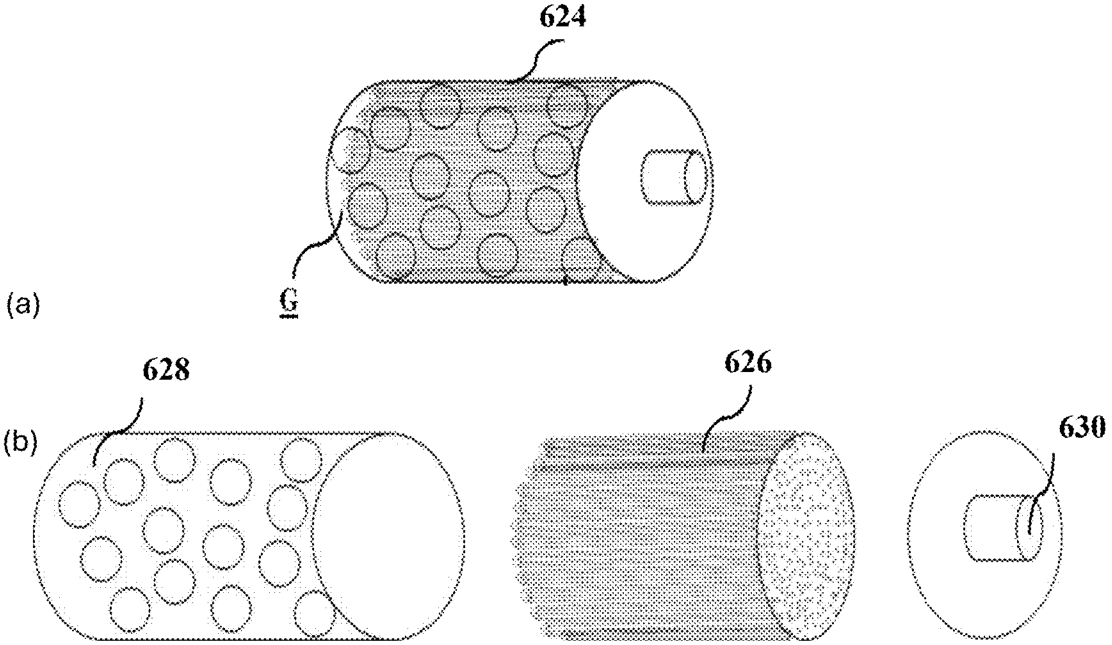
FIG. 6C illustrates a schematic of hollow fiber membrane as a permeability module, according to one or more embodiments.

The permeability module may comprise a hollow fiber membrane. As shown in FIG. 6C, a hollow fiber membrane 624 comprises numerous thin, flexible fibers 626 bundled together in a casing 628. Each fiber has a hollow core, allowing fluid to flow through. Both ends of the fibers on the right side and the left side of the fibers are U shaped.

In one embodiment, the hollow fiber membrane is a forward osmosis membrane and comprises an inlet end facing the first end of the device and an outlet facing towards a sensor module. These membranes utilize the natural osmosis process, where fluid moves from a low concentration to a high concentration through the membrane. Natural osmosis requires lower energy compared to traditional reverse osmosis systems that operate under lower pressure conditions within hollow fibers.

In an embodiment, one or more hollow fibers are made up of semipermeable membranes. In an embodiment, the hollow fibers may be surrounded by a high concentrated glucose solution (G) as shown in the figure. The high concentration of the glucose solution allows natural osmosis to happen within the device. As fluid ingress flows from the body into the permeability module, an almost equal volume of the glucose solution will be pushed out from the permeability module through the opening at the second end (630) of the module. The hollow fiber forward osmosis membranes are thin and flexible.

The permeability module 622 may comprise a semipermeable membrane and an osmotic agent chamber. The permeability module 622 allows ingress flow of fluid to an osmotic agent chamber and generates osmotic pressure. The fluid may be a bodily fluid. The fluid may enter the osmotic agent chamber from outside the AIMD through the semipermeable membrane. The osmotic pressure is generated in response to the ingress flow of the fluid. The osmotic pressure drives the piston to move longitudinally towards the one or more orifices in addition to the actuation of the motor. The osmotic pressure acts as an additional force. The osmotic pressure is directly proportionate to the movement of the piston longitudinally. The ingress flow of the fluid may also trigger the actuation of the motor. In such a case, the ingress flow of the fluid may control the discharge of the drug.

Figure 7:
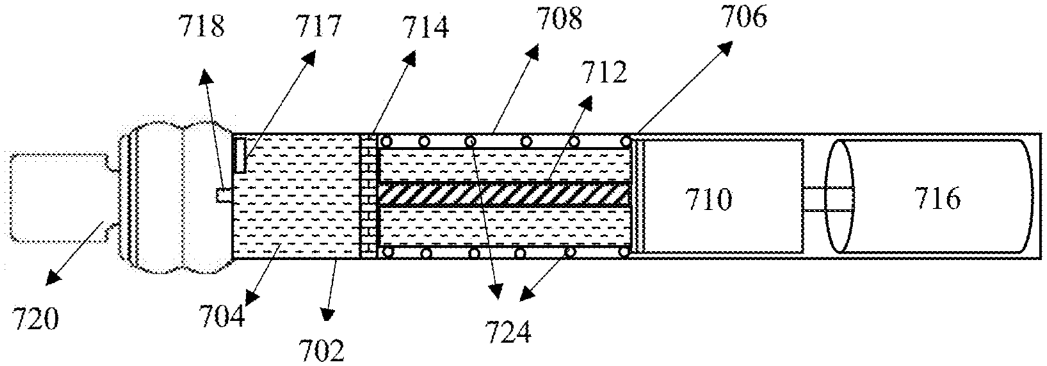
FIG. 7 illustrates an AIMD comprising one or more provisions on a motor chamber to allow flow of interstitial fluid and prevent creation of vacuum, according to one or more embodiments.

FIG. 7 illustrates an AIMD comprising one or more provisions on a motor chamber to allow flow of interstitial fluid and prevent creation of vacuum, according to one or more embodiments. The AIMD in FIG. 7 is similar to the one shown in FIG. 1. The other components (such as drug chamber 702, drug 704, motor chamber 706, housing 708, motor 710, driving component 712, piston 714, electronic module 716, sensor module 717, one or more orifices 718, check valve 720) of the AIMD are already explained in FIG. 1. The AIMD shown in FIG. 7 comprises the one or more provisions 724 on the housing (outer surface) of the motor chamber 706 in addition to the AIMD shown in FIG. 1. The housing of the motor chamber 706 comprises the one or more provisions 724. The housing of the motor chamber 706 may also comprise filters along with the one or more provisions 724. The one or more provisions 724 may be holes.

Figure 8:
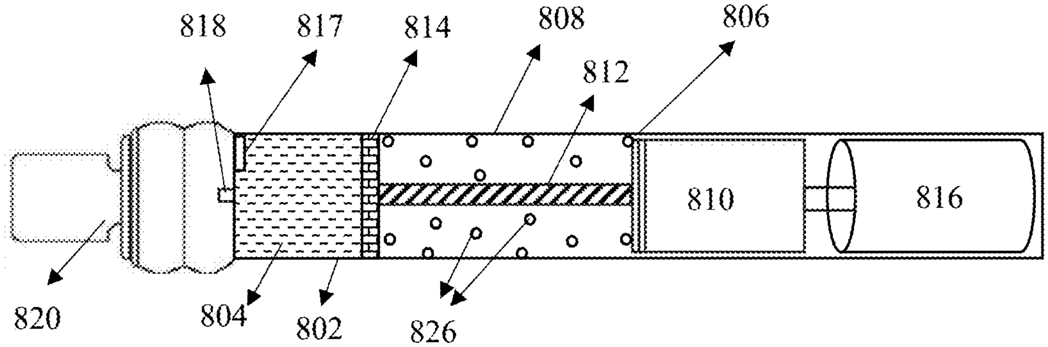
FIG. 8 illustrates an AIMD that pressurizes gas on a motor chamber to prevent creation of vacuum, according to one or more embodiments.

FIG. 8 illustrates an AIMD that pressurizes gas 826 on a motor chamber to prevent creation of vacuum, according to one or more embodiments. The other components (such as drug chamber 802, drug 804, motor chamber 806, housing 808, motor 810, driving component 812, piston 814, electronic module 816, sensor module 817, one or more orifices 818, check valve 820) of the AIMD are already explained in FIG. 1. The displacement of piston within the AIMD may lead to creation of vacuum which needs to be prevented. The creation of vacuum within the AIMD incurs risks such as cavitation risks, pressure differential risks, biocompatibility risks, outgassing risks, etc. If a vacuum environment is inadvertently created or leaks inside a sealed chamber within the AIMD, it could lead to cavitation risks such as structural failures or implosions. The vacuum inside the device can create pressure differential risks such as pressure imbalances that might lead to damage or reduced functionality. The vacuum can also lead to biocompatibility risks such as affecting the encapsulating materials or causing microcracks, potentially leading to exposure of internal components to the body. The vacuum may also interfere with pressure inside the AIMD that affects the operation of certain components. Further any residual vacuum in materials could release trapped gases over time, potentially interfering with AIMD performance or causing localized tissue reactions. The AIMD is designed in such a way to prevent creation of vacuum within the AIMD.

The electronic module may trigger opening a gas storage chamber (not shown) based on a signal received from the sensor module. The sensor module upon monitoring the displacement of the piston may communicate the signal to open the gas storage chamber. The gas storage chamber may be affixed externally to the AIMD. The gas storage chamber may comprise a valve that introduces the gas 826 into the AIMD. The pressure of the gas 826 may be varied (e.g., increased or decreased) by adjusting the regulator of the valve. The AIMD may use microvalves or elastomeric membranes to adjust internal pressure dynamically. The gas 826 may expand and occupy the area that is created due to the displacement of the piston. The gas 826 expands and restricts the creation of vacuum within the AIMD.

Figure 9:
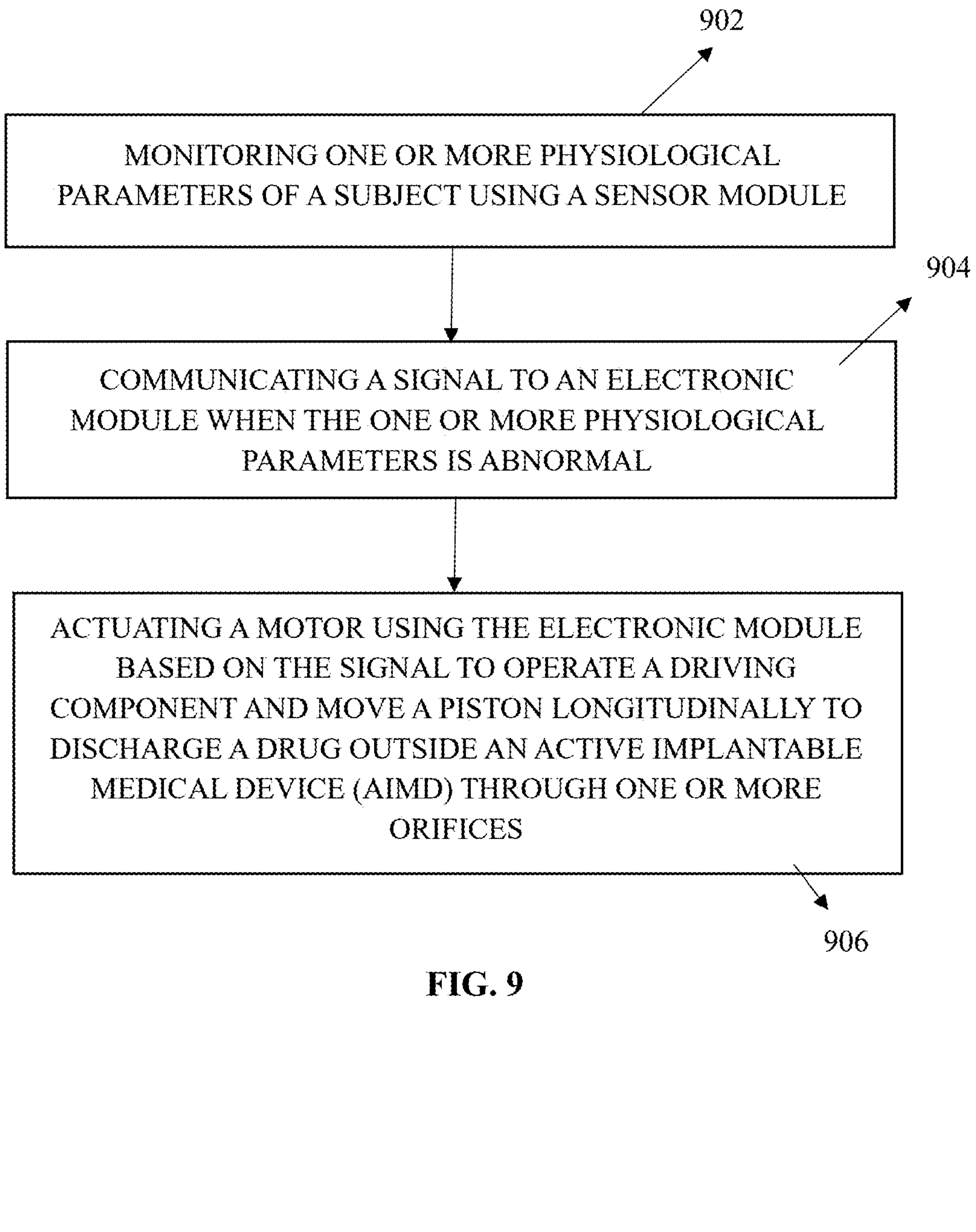
FIG. 9 illustrates a method of actuating a motor and discharging a drug, according to one or more embodiments.

FIG. 9 illustrates a method of actuating a motor and discharging a drug, according to one or more embodiments. The method comprises the following technical steps. At step 902, one or more physiological parameters of a subject are monitored using a sensor module. At step 904, a signal is communicated to an electronic module when the one or more physiological parameters is abnormal. At step 906, a motor is actuated using the electronic module based on the signal to operate a driving component and move a piston longitudinally to discharge a drug to a subject outside an active implantable medical device (AIMD) through one or more orifices.

The one or more physiological parameters are monitored continuously. The sensor module may be affixed to appropriate regions onto the subject. The sensor module may be placed within the subject. The sensor module may be communicatively coupled to the AIMD. The sensor communicates the signal to an electronic module when the one or more physiological parameters is abnormal. The electronic module actuates the motor. The motor upon actuation operates a driving component and moves a piston longitudinally to discharge a drug to a subject outside an active implantable medical device (AIMD) through one or more orifices.

Figure 10:
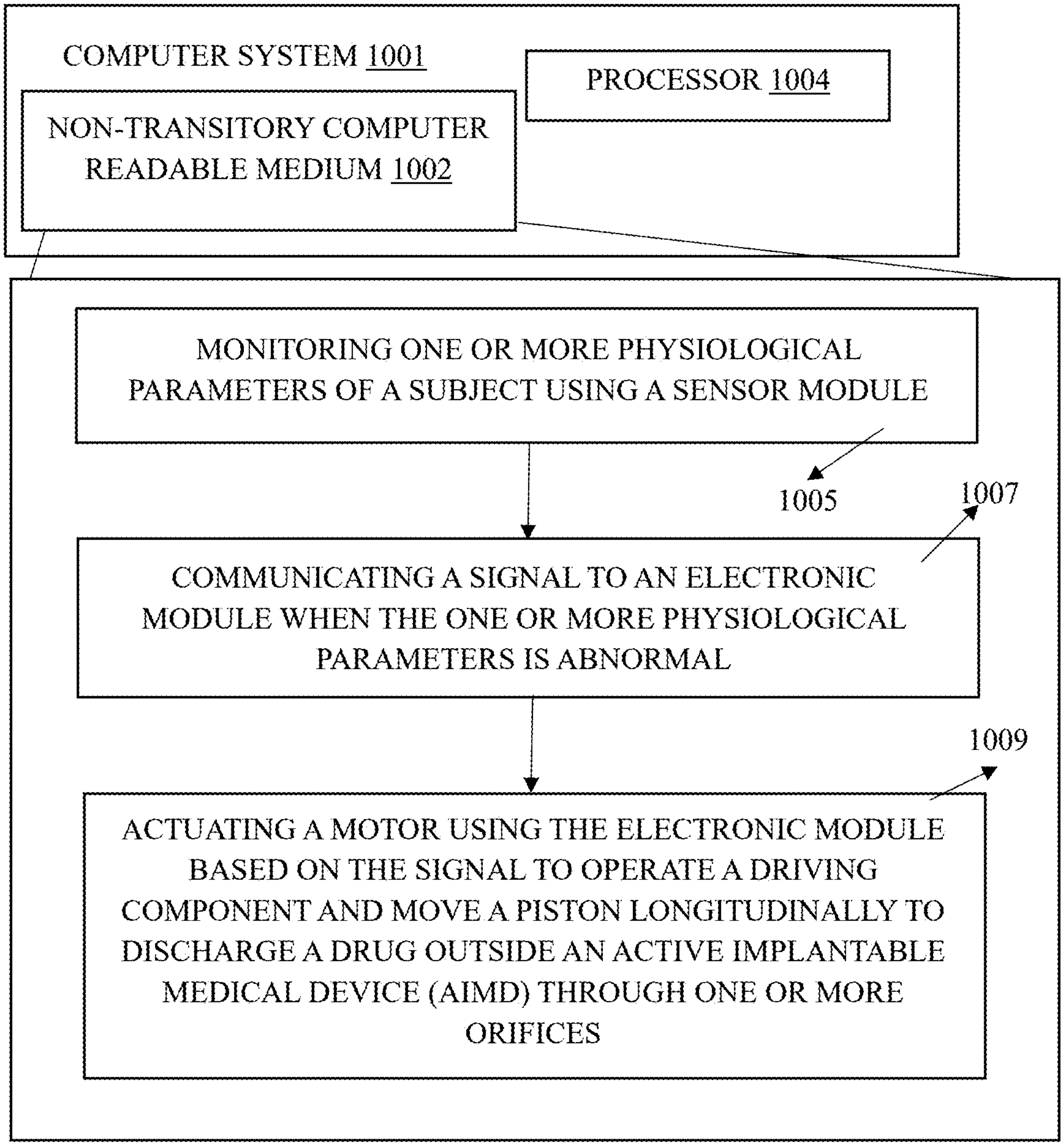
FIG. 10 illustrates a non-transitory computer readable storage medium, according to one or more embodiments.

FIG. 10 illustrates a non-transitory computer readable storage medium, according to one or more embodiments. According to an embodiment, disclosed is a computer system 1001 comprising the non-transitory computer readable storage medium 1002 having stored thereon instructions executable by a processor 1004 to perform operations comprising: monitoring one or more physiological parameters of a subject using a sensor module (at step 1005); communicating a signal to an electronic module when the one or more physiological parameters is abnormal (at step 1007); and actuating a motor using the electronic module based on the signal to operate a driving component and move a piston longitudinally to discharge a drug to the outside of an active implantable medical device (AIMD) through one or more orifices (at step 1009). The sensor module may be placed within the subject. The sensor module may be communicatively coupled to the AIMD.

Industrial Applicability: The industrial applicability of the active implantable medical device (AIMD) lies in its potential use in the medical device industry, particularly in the fields of drug delivery systems and implantable medical devices. This AIMD can be used to provide precise, controlled, and long-term drug administration for patients with chronic conditions or requiring sustained treatment, offering significant benefits for personalized medicine. The device's application is suitable for both human healthcare and veterinary medicine, allowing for customized drug release, which could improve patient outcomes and enhance compliance by reducing the need for manual intervention. Additionally, this technology could be utilized in biopharmaceutical manufacturing for developing devices that ensure accurate and efficient drug dosing for various therapeutic areas, including pain management, hormone replacement, cancer treatment, and other long-term therapies. Its miniaturized, automated drug delivery mechanism makes it especially relevant for industries focused on creating devices that are both compact and highly effective, meeting the growing demand for implantable and wearables in healthcare.

In one aspect, a wearable drug delivery system is described. The wearable drug delivery system is configured for controlled and sustained release of therapeutic agents through the skin. The wearable drug delivery system comprises an active wearable medical device (AWMD), a drug outlet, a fluid chamber containing a fluid (e.g., water) to support osmosis within the active wearable medical device (AWMD), a channel (e.g., microfluidic distribution channel) fluidically connected to a drug outlet, a plurality of microneedles fluidically connected to the microfluidic channel for drug delivery into the skin, and an attachment component for securing the system to the skin. The active wearable medical device (AWMD) is not implanted in a body of the mammal. Instead, the active wearable medical device (AWMD) is secured to the skin of the mammal for controlled release of therapeutic agents through the skin. The AWMD may be one of a flat shape, a tubular shape, a cylindrical shape, a disc shape, a capsule shape, a coil shape, a sheet shape, a film shape, etc.

The AWMD including other components includes a permeability module, a piston, a drug chamber, a valve module, a sensor module, an electronic module and a machine learning model. Without limitation, positioning of modules, part or other components in AWMD could be arranged in a fashion as described in one or more embodiments of this disclosure.

In one embodiment, the wearable drug delivery system comprises an attachment component having perforations adapted to secure the system to skin and to ensure stable contact with the skin during the discharge of the drug. The attachment component may be one of an adhesive layer, a mechanical fastener, a wearable strap, a wearable band, and a skin micro-anchor. In another embodiment, the attachment component comprises an adhesive layer.

In one embodiment, the fluid chamber is an active operated chamber. The active operated chamber requires an external power source to operate and pump or release the fluid. The active operated chamber involves electronic or mechanical components. In another embodiment, the fluid chamber is a passive operated chamber. The passive operated chamber does not require external power to function. It relies on external forces (like pressure, diffusion, or gravity) to operate and pump or release the fluid.

In one embodiment, the channel (e.g., microfluidic distribution channel) comprises a catheter configured to deliver the drug to a specific anatomical site. The catheter is configured for targeted administration of the drug. The channel comprises a biocompatible material. In one embodiment, the channel comprises a dissolvable material that naturally dissolves in the body over a period of time. The dissolvable materials dissolves fully eliminating risk of needle-stick injury. The channel can distribute or mix multiple drugs or reagents in a defined sequence.

In one embodiment, the system comprises a plurality of drug chambers. The plurality of drug chambers is configured to store and deliver multiple drug formulations separately or sequentially. In this embodiment, the wearable drug delivery system is configured to switch between the plurality of drug chambers for sequential discharge of the drug or combination of discharge of the drug. Each drug chamber contains a specific drug or dose and is fluidically connected to a common delivery pathway (e.g., microneedles, catheter, nozzle, etc.). Each drug chamber may be prefilled with a specific therapeutic agent. The selected drug chamber releases its contents through a shared or dedicated outlet to the target site (e.g., skin, tissue, bloodstream). The plurality of drug chambers can be activated one after the other or together, depending on treatment needs (e.g., time-based, responsive to sensors, etc.). The plurality of drug chambers allows combination therapy (e.g., insulin+GLP-1, vaccine+adjuvant) in a single device. The plurality of drug chambers further enables time-controlled or programmable dosing (e.g., hourly, daily). The physical separation between the plurality of drug chambers prevents chemical interactions between incompatible drugs. The plurality of drug chambers may have primary chambers and backup chambers. Backup chambers can enhance reliability if a primary chamber fails. The concept of the the plurality of drug chambers reduces the need for multiple injections or devices.

Figure 11A:
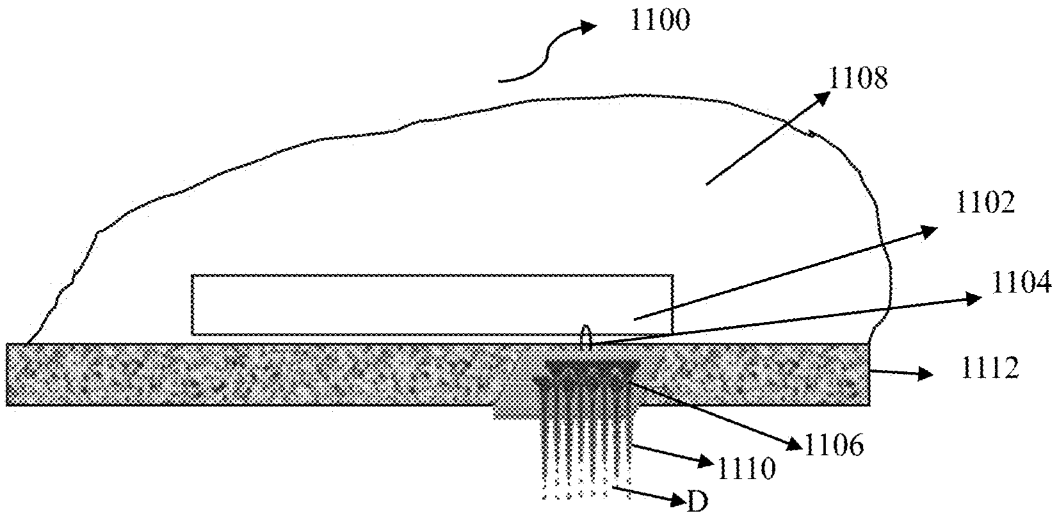
FIGS. 11A and 11B illustrate a schematic representation of a wearable drug delivery system comprising an active wearable medical device (AWMD), according to one or more embodiments.
Figure 11B:
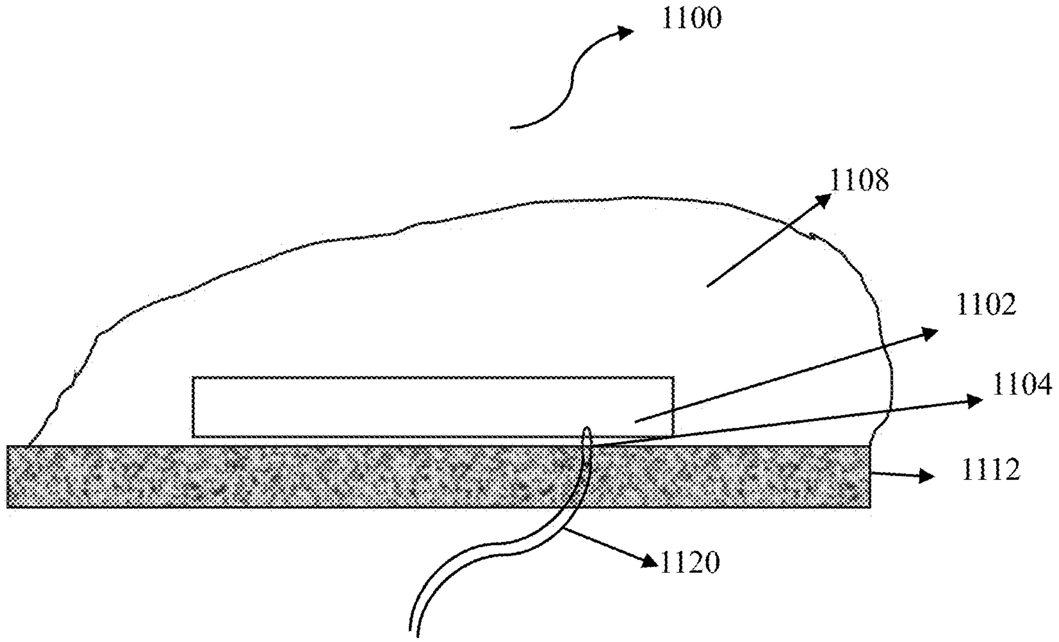

In one embodiment, the wearable drug delivery system comprises a real-time imaging and navigation guidance device. The real-time imaging and navigation guidance device is configured to aid placement of the catheter and monitor dispersion of the drug in real-time. The real-time imaging and navigation guidance device is used to enhance the accuracy, safety, and effectiveness of catheter-based procedures—particularly for precise placement and targeted drug dispersion within the body. The real-time imaging and navigation guidance device guides the clinician or robotic arm to insert and advance the catheter through complex vascular or anatomical paths. Feedback ensures precise tip positioning at or near the therapeutic target (e.g., tumor, blood clot, nerve bundle). The real-time imaging and navigation guidance device is further utilized to track volume, diffusion, and retention of the drug in the target zone, optimizing therapy. The real-time imaging and navigation guidance device enables accurate catheter placement and controlled drug delivery. The real-time imaging and navigation guidance device reduces risk of damage to healthy tissue or vessels. The real-time imaging and navigation guidance device allows immediate adjustment during procedure. The real-time imaging and navigation guidance device is configured to ensure that the drug reaches the intended location in optimal concentration. The real-time imaging and navigation guidance device is further configured to minimize off-target effects or catheter misplacement and enhance therapeutic effectiveness and patient safety FIGS. 11A and 11B illustrate a schematic representation of the wearable drug delivery system 1100 comprising an active wearable medical device (AWMD) 1102, according to one or more embodiments. In FIG. 11A, the wearable drug delivery system 1100 comprises (1) an active wearable medical device (AWMD) 1102, (2) a fluid chamber 1108, and (3) a channel 1106. The active wearable medical device (AWMD) 1102 comprises a drug chamber, a motor chamber, a piston, an electronic module, and a permeability module. The drug chamber comprises a drug. The motor chamber comprises a housing, a motor, and a driving component. The piston is affixed to a first end of the driving component. The electronic module actuates the motor to operate the driving component and move the piston longitudinally to discharge the drug outside the active wearable medical device (AWMD) 1102 through one or more orifices. The permeability module allows passive ingress flow of a fluid to an osmotic agent chamber from the fluid chamber 1108 through a semipermeable membrane upon activation of the fluid chamber 1108 and generates osmotic pressure to drive the piston longitudinally towards the one or more orifices in addition to actuation of the piston by the motor. The fluid chamber 1108 contains the fluid. The channel 1106 is fluidically coupled to a drug outlet 1104 wherein the channel 1106 discharges and deliver the drug. The channel 1106 is microfluidic distribution channel. According to an embodiment, the active wearable medical device (AWMD) 1102 is not implanted in a body of a mammal and is fluidically coupled to the fluid chamber 1108 via the semipermeable membrane.

The active wearable medical device (AWMD) 1102 comprises the drug outlet 1104 positioned to ensure uniform flow of drug into the channel 1106 (e.g., microfluidic distribution channel). the fluid chamber 1108, containing a fluid (e.g., water), supports an osmotic gradient that generates osmotic pressure. This osmotic pressure actuates the piston within the active wearable medical device (AWMD) 1102, which displaces the drug D from the drug chamber through an electronically controlled valve module. The valve module permits one-way drug flow based on real-time displacement data from a sensor module (not shown). The channel 1106 is fluidically connected to the drug outlet 1104 and to a plurality of microneedles 1110, which enable precise and uniform transdermal drug delivery. Each microneedle of the plurality of microneedles 1110 is designed to penetrate the stratum corneum without reaching pain receptors, allowing painless administration. The channel 1106 and the plurality of microneedles 1110 may be fabricated from biocompatible materials such as silicon, polymers, or metals. An adhesive layer 1112 is disposed on the underside of the wearable drug delivery system 1100. The adhesive layer 1112 comprises a biocompatible adhesive backing with optional perforations for breathability, ensuring stable contact during drug administration.

In an embodiment, the active wearable medical device (AWMD) 1102 may be drug-filled or may be configured to receive a prefilled drug chamber that is inserted or connected into the device. The active wearable medical device (AWMD) 1102 may have a defined shape comprising one of cylindrical, circular, or oval geometries, and may incorporate ergonomic features such as rounded corners and low profiles.

In an embodiment, the active wearable medical device (AWMD) 1102 may include a sensor to provide feedback to the device. This sensor may include, for example, a glucose sensor or other biosensors that monitor physiological parameters in real-time and provide feedback to the active wearable medical device (AWMD) 1102. The active wearable medical device (AWMD) 1102 discharges the drug based on the real-time feedback. The active wearable medical device (AWMD) 1102 is designed to administer the drug based on individual patient needs. The AWMD 1102 is programmed to discharge the drug in response to patient-specific parameters.

FIG. 11B illustrates the wearable drug delivery system of FIG. 11A wherein the drug outlet 1104 is fluidically connected to a catheter 1120 for targeted drug administration to a specific anatomical site. The plurality of microneedles 1110 in FIG. 11A is replaced with the catheter 1120 in FIG. 11B.

In one embodiment, the fluid chamber is an expandable elastomeric bladder. The expandable elastomeric bladder expands and gradually releases the fluid across the semipermeable membrane to generate the osmotic pressure when a pressure is applied to the expandable elastomeric bladder. In this embodiment, the wearable drug delivery system comprises an expandable elastomeric bladder configured as the fluid chamber for storing the fluid (e.g., water) or another biocompatible aqueous medium. The expandable elastomeric bladder is in fluidic communication with a semipermeable membrane that separates it from the osmotic agent chamber of the active wearable medical device. As fluid pressure is applied—either pre-filled or generated passively during wear—the bladder expands and gradually releases fluid (e.g., water) across the semipermeable membrane. This water mixes with the osmotic agent in the osmotic pump, generating pressure that drives a piston mechanism to deliver the drug through microneedles into the skin.

Figure 12A:
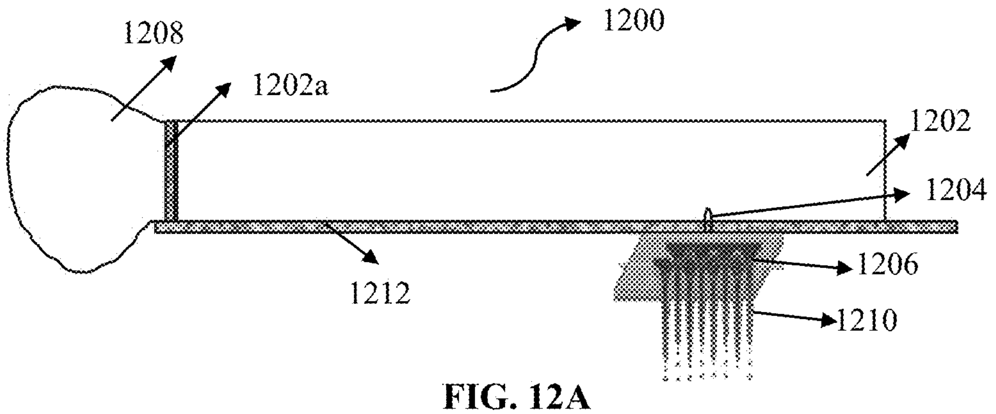
FIGS. 12A and 12B illustrate a wearable drug delivery system incorporating an expandable elastomeric bladder as the fluid chamber, according to one or more embodiments.
Figure 12B:
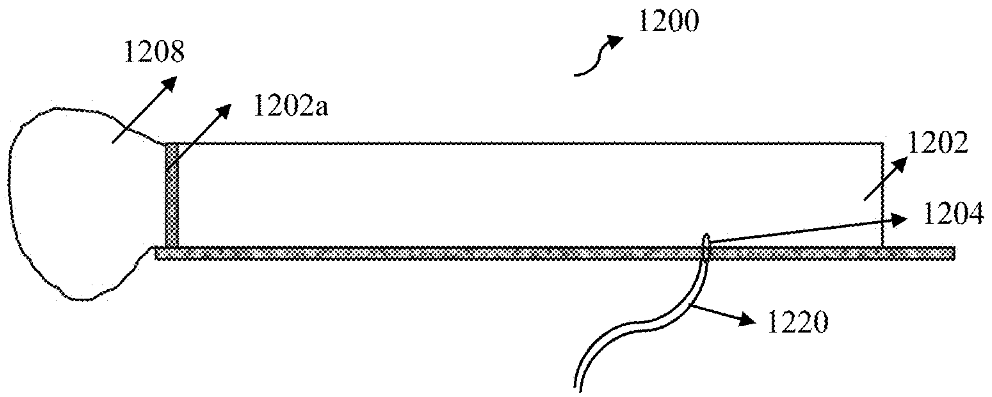

FIGS. 12A and 12B illustrate a wearable drug delivery system 1200 incorporating an expandable elastomeric bladder as the fluid chamber 1208, according to one or more embodiments. In FIG. 12A, the expandable elastomeric bladder, in fluidic contact with a semipermeable membrane 1202*a* of the active wearable medical device (AWMD) 1202, stores a biocompatible aqueous medium. The bladder may be either actively operated or passively operated. The bladder may be passively operated via an elastic recoil. The bladder may be actively operated using sensors or controllers that regulates outlet of the bladder. Upon activation, the fluid pressure is applied and the water is released across the semipermeable membrane into the osmotic pump, generating osmotic pressure that actuates a piston. The piston drives the drug through a valve module and drug outlet 1204 into a microfluidic distribution channel 1206, which is connected to a plurality of microneedles 1210 for delivering drug into the skin. An adhesive layer 1212 ensures skin attachment and breathability.

In an embodiment, the active wearable medical device (AWMD) 1202 may be drug-filled or may be configured to receive a prefilled drug chamber that is inserted or connected into the device. The active wearable medical device (AWMD) 1202 may have a defined shape comprising one of cylindrical, circular, or oval geometries, and may incorporate ergonomic features such as rounded corners and low profiles.

In an embodiment, the active wearable medical device (AWMD) 1202 may include a sensor to provide feedback to the device. This sensor may include, for example, a glucose sensor or other biosensors that monitor physiological parameters in real-time and provide feedback to the active wearable medical device (AWMD) 1102. The active wearable medical device (AWMD) 1202 discharges the drug based on the real-time feedback. The active wearable medical device (AWMD) 1202 is designed to administer the drug based on individual patient needs. The AWMD 1202 is programmed to discharge the drug in response to patient-specific parameters.

FIG. 12B illustrates the wearable drug delivery system of FIG. 12A comprising an expandable elastomeric bladder, wherein the drug outlet 124 is connected to catheter 1220 for localized drug delivery. The plurality of microneedles 1210 in FIG. 12A is replaced with the catheter 1220 in FIG. 12B.

In another embodiment, the fluid chamber is a rigid reservoir that enables diffusion of the fluid across the semipermeable membrane to dissolve an osmotic agent in the osmotic agent chamber and generate an osmotic gradient to drive the piston. In this embodiment, the wearable drug delivery system comprises a rigid reservoir, such as a molded polymer or metal container, configured to passively store water. The rigid reservoir is fluidically connected to the osmotic agent chamber via a flow-regulating semipermeable membrane or capillary channel that allows controlled diffusion of water. As the osmotic agent dissolves, water is drawn from the rigid reservoir, generating an osmotic gradient that activates the osmotic pump. This design ensures mechanical stability and consistent osmotic flow for controlled drug delivery.

Figure 13A:
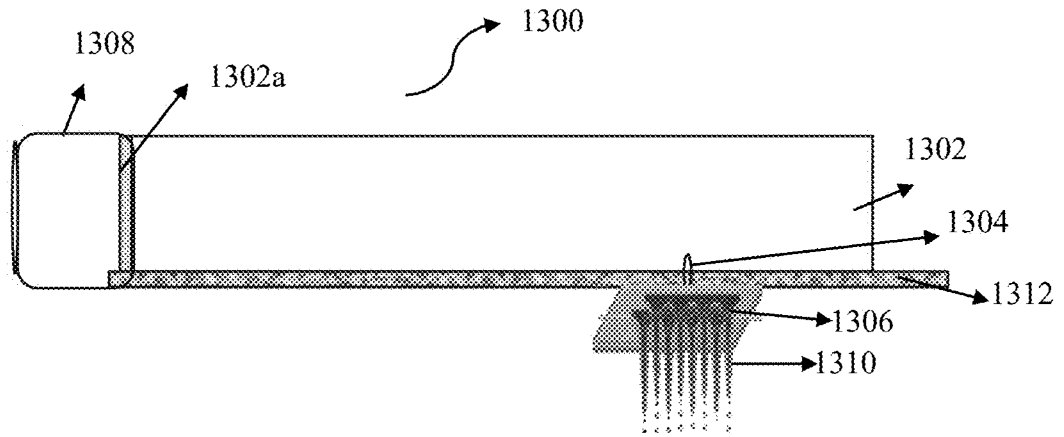
FIGS. 13A and 13B illustrate a wearable drug delivery system incorporating a rigid reservoir as the fluid chamber, according to one or more embodiments.
Figure 13B:
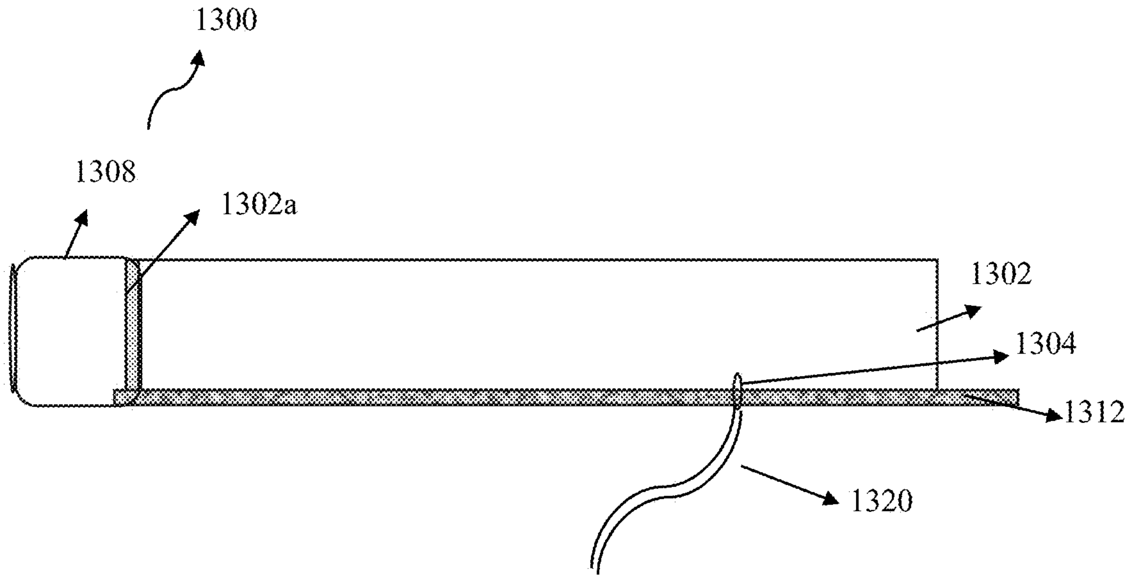

FIGS. 13A and 13B illustrate a wearable drug delivery system 1300 incorporating a rigid reservoir as the fluid chamber 1308, according to one or more embodiments. The rigid reservoir may be made of molded polymer or metal. In FIG. 13A, the rigid reservoir is fluidically connected to the osmotic agent chamber of the active wearable medical device (AWMD) 1302 via the semipermeable membrane 1302*a*. As the osmotic agent dissolves, osmotic pressure builds and actuates a piston, which displaces the drug through a valve module and drug outlet 1304 into the channel 1306 (e.g., microfluidic distribution channel) connected to microneedles 1310 for transdermal delivery. An adhesive layer 1312 secures the system to the skin.

In an embodiment, the active wearable medical device (AWMD) 1302 may be drug-filled or may be configured to receive a prefilled drug chamber that is inserted or connected into the device. The active wearable medical device (AWMD) 1302 may have a defined shape comprising one of cylindrical, circular, or oval geometries, and may incorporate ergonomic features such as rounded corners and low profiles.

In an embodiment, the active wearable medical device (AWMD) 1302 may include a sensor to provide feedback to the device. This sensor may include, for example, a glucose sensor or other biosensors that monitor physiological parameters in real-time and provide feedback to the active wearable medical device (AWMD) 1302. The active wearable medical device (AWMD) 1302 discharges the drug based on the real-time feedback. The active wearable medical device (AWMD) 1302 is designed to administer the drug based on individual patient needs. The AWMD 1302 may be programmed to discharge the drug in response to patient-specific parameters.

FIG. 13B illustrates the wearable drug delivery system of FIG. 13A incorporating a rigid fluid reservoir, wherein the drug outlet 1304 is connected to a catheter 1320 for directing the drug to a selected tissue region. The plurality of microneedles 1310 in FIG. 13A is replaced with the catheter 1320 in FIG. 13B.

In another embodiment, the fluid chamber is a hydrogel reservoir. The hydrogel reservoir comprises a hydrogel that releases the fluid over time to enable the passive ingress flow of the fluid to the osmotic agent chamber from the hydrogel reservoir. In this embodiment, the wearable drug delivery system comprises a hydrogel reservoir as the fluid chamber, wherein a pre-hydrated, biocompatible hydrogel matrix serves as a solid-state water source. The hydrogel reservoir is positioned adjacent to a semipermeable membrane that interfaces with the osmotic agent chamber. Over time, water is gradually released from the hydrogel and diffuses through the semipermeable membrane, dissolving the osmotic agent and generating osmotic pressure to actuate the piston and enable drug delivery. This configuration reduces the presence of free liquid, making it suitable for compact, flexible, and patch-style systems.

Figure 14A:
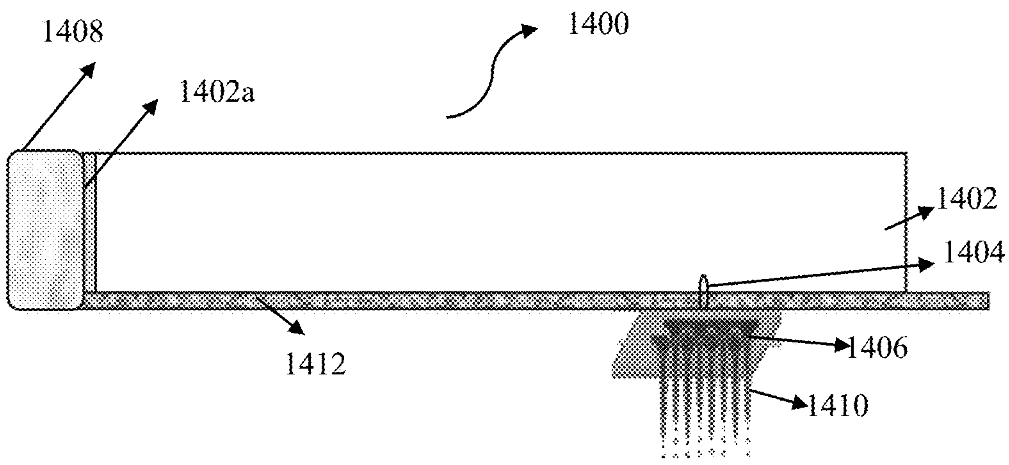
FIGS. 14A and 14B depict a wearable drug delivery system incorporating a hydrogel reservoir as the fluid chamber, according to one or more embodiments.
Figure 14B:
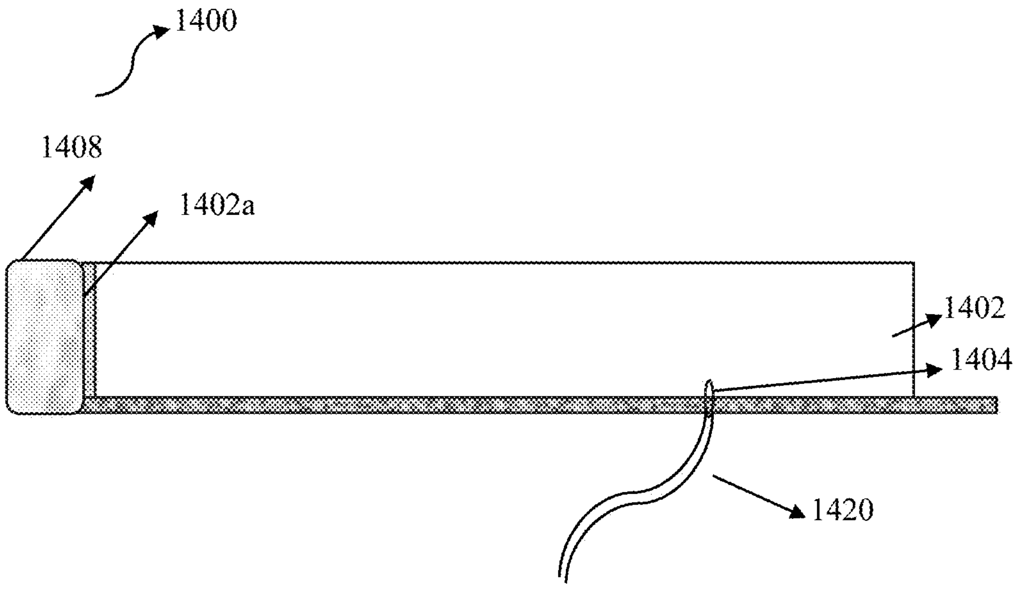

FIGS. 14A and 14B depict a wearable drug delivery system 1400 incorporating a hydrogel reservoir as the fluid chamber 1408, according to one or more embodiments. In FIG. 14A, the hydrogel reservoir is pre-hydrated and biocompatible, and positioned adjacent to the semipermeable membrane 1402*a* of the active wearable medical device (AWMD) 1402. Water released from the hydrogel activates the osmotic pump, generating pressure that actuates a piston to displace the drug through a valve module and drug outlet 1404 into the channel 1406 (e.g., microfluidic distribution channel). The channel 1406 leads to the plurality of microneedles 1410 for painless transdermal delivery. An adhesive layer 1412 ensures skin attachment and breathability.

In an embodiment, the active wearable medical device (AWMD) 1402 may be drug-filled or may be configured to receive a prefilled drug chamber that is inserted or connected into the active wearable medical device (AWMD) 1402. The active wearable medical device (AWMD) 1402 may have a defined shape comprising one of cylindrical, circular, or oval geometries, and may incorporate ergonomic features such as rounded corners and low profiles.

In an embodiment, the active wearable medical device (AWMD) 1402 may include a sensor to provide feedback to the device. This sensor may include, for example, a glucose sensor or other biosensors that monitor physiological parameters in real-time and provide feedback to the active wearable medical device (AWMD) 1402. The active wearable medical device (AWMD) 1402 discharges the drug based on the real-time feedback. The active wearable medical device (AWMD) 1402 is designed to administer the drug based on individual patient needs. The AWMD 1402 may be programmed to discharge the drug in response to patient-specific parameters.

FIG. 14B illustrates the wearable drug delivery system of FIG. 14A incorporating a hydrogel-based fluid chamber, wherein the drug outlet is fluidically connected to a catheter 1420 for targeted therapeutic delivery. The plurality of microneedles 1410 in FIG. 14A is replaced with the catheter 1420 in FIG. 14B.

In another embodiment, the fluid chamber is a microfluidic reservoir. The microfluidic reservoir is integrated with a flow restrictor interfaced with the semipermeable membrane to deliver the fluid to the osmotic agent chamber at a controlled rate. The microfluidic reservoir is configured to contain water and integrated with a flow restrictor, such as a nanochannel, porous membrane, or precision orifice. The flow restrictor interfaces with a semipermeable membrane leading to the osmotic agent chamber of a drug delivery pump, delivering the fluid (e.g., water) at a controlled rate to sustain osmotic pressure over an extended period. This configuration enables precise control of fluid delivery matched to the expected osmotic uptake rate and dosing schedule.

Figure 15A:
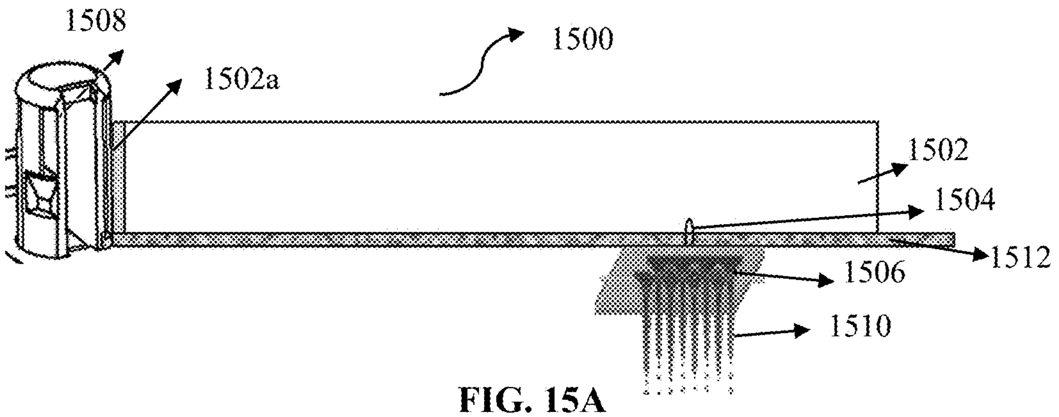
FIGS. 15A and 15B illustrate a wearable drug delivery system incorporating a microfluidic reservoir as the fluid chamber, according to one or more embodiments.
Figure 15B:
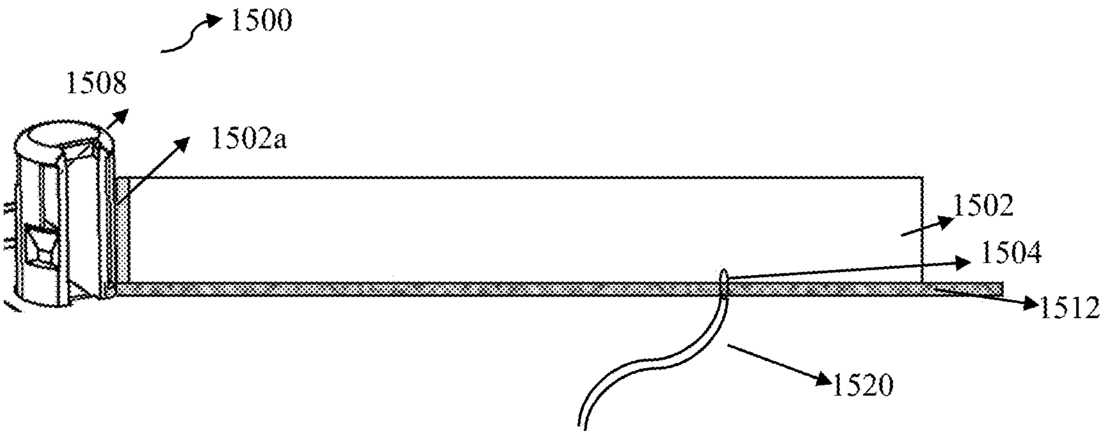

FIGS. 15A and 15B illustrate a wearable drug delivery system 1500 incorporating a microfluidic reservoir as the fluid chamber 1508, according to one or more embodiments. The microfluidic reservoir may be integrated with a flow restrictor. The flow restrictor may include a nanochannel, porous membrane, or precision orifice. In FIG. 15A, the flow restrictor is in fluidic communication with a semipermeable membrane 1502*a* of the active wearable medical device (AWMD) 1502 leading to the osmotic agent chamber. The resulting osmotic pressure actuates a piston of the active wearable medical device (AWMD) 1502, which drives drug flow through a valve module (not shown in the figure) and drug outlet 1504 into the channel 1506 (e.g., microfluidic distribution channel). The drug is subsequently delivered via the plurality of microneedles 1510 into the skin. An adhesive layer 1512 secures the wearable drug delivery system 1500 during use.

In an embodiment, the active wearable medical device (AWMD) 1502 may be drug-filled or may be configured to receive a prefilled drug chamber that is inserted or connected into the active wearable medical device (AWMD) 1502. The active wearable medical device (AWMD) 1502 may have a defined shape comprising one of cylindrical, circular, or oval geometries, and may incorporate ergonomic features such as rounded corners and low profiles.

In an embodiment, the active wearable medical device (AWMD) 1502 may include a sensor to provide feedback to the device. This sensor may include, for example, a glucose sensor or other biosensors that monitor physiological parameters in real-time and provide feedback to the active wearable medical device (AWMD) 1502. The active wearable medical device (AWMD) 1502 discharges the drug based on the real-time feedback. The active wearable medical device (AWMD) 1502 is designed to administer the drug based on individual patient needs. The AWMD 1502 may be programmed to discharge the drug in response to patient-specific parameters.

FIG. 15B illustrates the wearable drug delivery system of FIG. 15A comprising a microfluidic reservoir with flow restrictor, wherein the drug outlet 1504 is connected to a catheter 1520 to facilitate precise regional drug administration. The plurality of microneedles 1510 in FIG. 15 is replaced with the catheter 1520 in FIG. 15B.

An embodiment relates to the drug delivery system for targeted drug administration. The drug delivery system comprises a catheter and a drug delivery device configured to deliver a therapeutic agent through the catheter. The drug delivery device can be one of an active implantable medical device or an active wearable medical device. The drug delivery device comprises a drug chamber containing a drug formulation, an osmotic pump mechanism comprising an osmotic agent chamber, a semi-permeable membrane, and an actuator (e.g., a piston) that responds to osmotic pressure to displace the drug. A drug outlet is fluidically connected to the catheter. The catheter routes the drug to a specific anatomical site, such as a blood vessel, organ, or localized tissue region. The catheter may comprise an implantable, flexible microcatheter. The catheter may be made from biocompatible materials such as polyurethane or silicone. The catheter may include one or more delivery ports or diffusers at its distal end to facilitate uniform drug dispersion. This configuration enables localized or regional delivery, enhancing therapeutic efficacy and minimizing systemic exposure.

Figure 16:
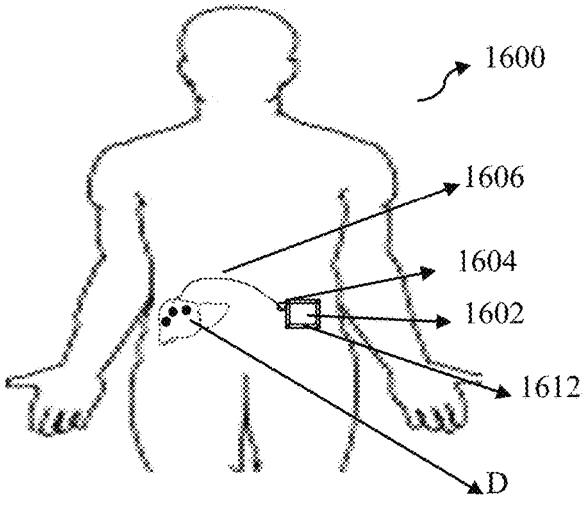
FIG. 16 illustrates a drug delivery system configured for targeted drug administration through a catheter, according to one or more embodiments.

FIG. 16 illustrates a drug delivery system 1600 configured for targeted drug administration through a catheter 1606, according to one or more embodiments. The drug delivery system 1600 comprises an active wearable medical device 1602 and the catheter 1606. The drug outlet 1604 of the active wearable medical device 1602 is fluidically connected to a catheter 1606. The catheter 1606 is configured to deliver the drug D to a targeted anatomical site (e.g., liver) (as shown in FIG. 16). The catheter 1606 may comprise delivery ports or diffusers at its distal end. An adhesive 1612 may be included to maintain system position with respect to the body of the mammal.

In an embodiment, the active wearable medical device (AWMD) 1602 may be drug-filled or may be configured to receive a prefilled drug chamber that is inserted or connected into the active wearable medical device (AWMD) 1602. The active wearable medical device (AWMD) 1602 may have a defined shape comprising one of cylindrical, circular, or oval geometries, and may incorporate ergonomic features such as rounded corners and low profiles.

In an embodiment, the active wearable medical device (AWMD) 1602 may include a sensor to provide feedback to the device. This sensor may include, for example, a glucose sensor or other biosensors that monitor physiological parameters in real-time and provide feedback to the active wearable medical device (AWMD) 1602. The active wearable medical device (AWMD) 1602 discharges the drug D based on the real-time feedback. The active wearable medical device (AWMD) 1602 is designed to administer the drug D based on individual patient needs. The AWMD 1602 may be programmed to discharge the drug D in response to patient-specific parameters.

In one aspect, the present disclosure relates to robotic surgical systems and methods for the robotic implantation of a drug delivery device implanted into a human body, and to alternative embodiments in which the drug delivery device is externally positioned on the patient's skin surface, with a transdermal catheter providing access to an internal target site for therapeutic delivery. The system comprises a robotic manipulator configured for minimally invasive surgical procedures to access a predetermined implantation site (e.g., specific anatomical site) within the body. The robotic manipulator may comprise a programmable, multi-jointed robotic arm capable of performing delicate dissection, pocket formation, and precise device placement under image-guided navigation.

In some embodiments, the system further comprises an implantable drug delivery device (AIMD) enclosed in a biocompatible housing, the housing containing an internal drug reservoir, a pumping mechanism associated electronic control circuitry, a power source, a catheter port, and optionally, a self-sealing refill port. In some embodiments, a flexible, biocompatible catheter is connected to the drug delivery device, the catheter being routed subcutaneously or through body tissue to deliver the therapeutic substance to a predetermined anatomical target, such as the intrathecal space, peritoneal cavity, intravascular system, or other tissue compartments. The catheter may be reinforced to resist kinking and may include additional features such as bacterial filters, check valves, and flow control regulators.

The robotic implantation method comprises a preoperative planning phase wherein patient-specific anatomical imaging (e.g., CT, MRI, or ultrasound) is utilized to identify an optimal implantation site and to plan the catheter route, avoiding critical anatomical structures. The robotic manipulator is then employed to gain minimally invasive access to the implantation region via small incisions and blunt tissue dissection. A subcutaneous or intraperitoneal pocket is then created robotically for receiving the drug delivery device housing. Following pocket creation, the implantable drug delivery device is delivered and positioned within the pocket, and the catheter is tunnelled and routed to the anatomical target site. The robotic system then secures the drug delivery device and catheter using sutures, adhesives, or mechanical anchors. Once the hardware is fixed in place, system integration is performed by connecting the device components and testing the device function, including delivery of a test bolus to confirm patency and proper placement. The incisions are then closed using minimally traumatic techniques such as fine suturing or tissue adhesives.

Robotic implantation offers numerous advantages, including enhanced precision of device and catheter placement, reduced tissue trauma due to controlled and delicate movements, and minimization of incision size. The programmable and automated nature of robotic operations also contributes to reproducibility, consistency, and a lower rate of complications compared to manual surgical techniques. Real-time intraoperative imaging and navigation further improve accuracy and safety. Collectively, these features result in reduced postoperative pain, accelerated patient recovery, and improved therapeutic outcomes.

In another embodiment, the drug delivery device is configured for external placement on the surface of the patient's skin, thereby obviating the need for surgical implantation of the device body. In this configuration, the system comprises an external drug delivery device adapted for skin attachment via medical-grade adhesive or mechanical fastening means. The external drug delivery device houses a drug reservoir, a pumping mechanism (peristaltic or metering type), electronic control circuitry, a power source, and an interface for refilling, programming, or monitoring. A transdermal catheter assembly connects to the external drug delivery device, and the catheter is inserted through the skin and routed to a desired subcutaneous, intramuscular, or intravascular site. The catheter is secured in place using a securement mechanism that may include mechanical anchors, adhesive pads, or antimicrobial dressings.

In some embodiments, operation of the external drug delivery device comprises programmed dosing via the pump, delivering medication directly to the target site through the transdermal catheter. The system may incorporate sensors to monitor flow rate, detect occlusion or leakage, and verify reservoir levels. The external configuration allows for non-invasive refilling, device replacement, or reprogramming, thereby reducing the need for follow-up surgical intervention. This embodiment provides benefits such as ease of use, simplified maintenance, and reduced risk of systemic infection, particularly at the catheter entry point, due to securement and barrier protection.

An exemplary embodiment of the system may comprise the following integrated components: (i) a robotic manipulator system for surgical access and device handling; (ii) an implantable or externally placed drug delivery device as described; (iii) a catheter for targeted drug delivery; (iv) an imaging and navigation system utilizing modalities such as fluoroscopy, ultrasound, or CT for intraoperative and preoperative guidance; (v) fixation and anchoring mechanisms including sutures, adhesives, or mechanical components for securing the drug delivery device and catheter; and (vi) optional feedback sensors for real-time monitoring of drug delivery parameters and device status.

Figure 17:
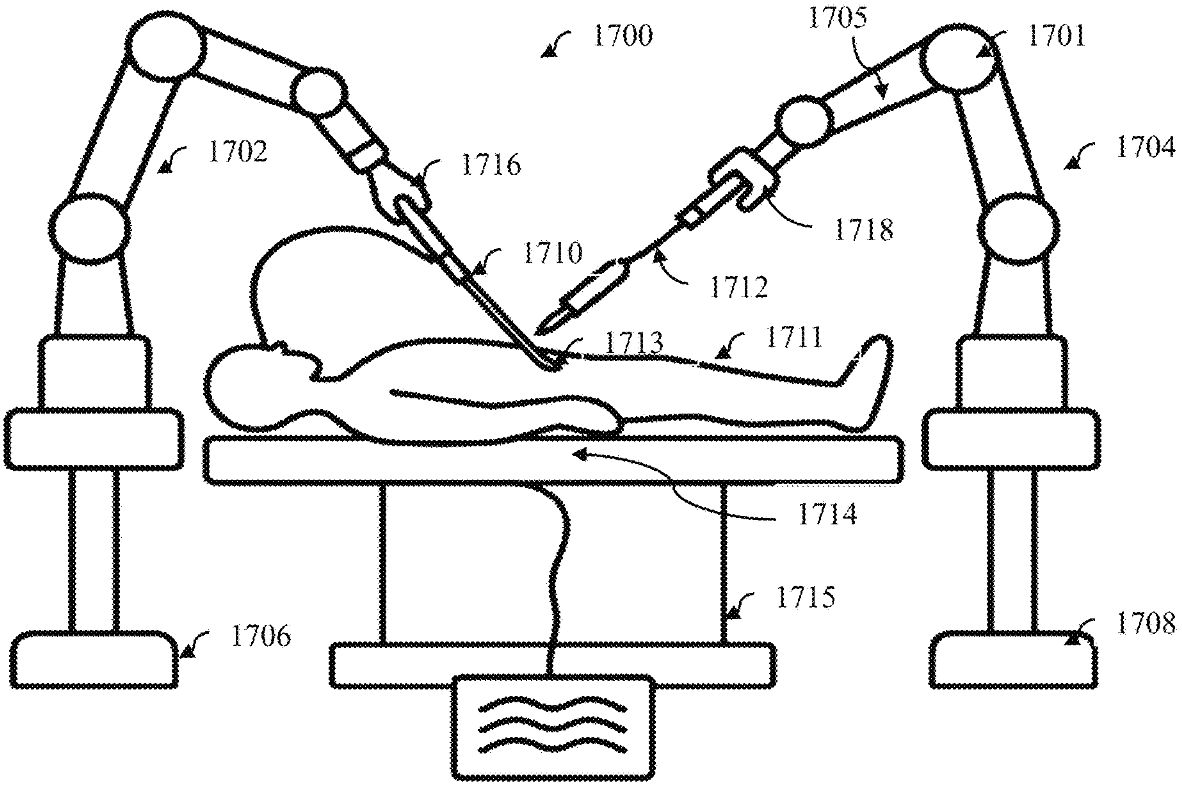
FIG. 17 illustrates a robotic surgical system configured for the implantation of an active implantable medical device, according to one or more embodiments.

FIG. 17 illustrates a robotic surgical system 1700 configured for the implantation of an active implantable medical device, according to one or more embodiments. The system comprises a first robotic arm 1702 and a second robotic arm 1704, each mounted on respective robot bases 1706 and 1708. These arms are equipped with end effectors, which may include robotic manipulators or grippers designed to handle endoscopic instruments and/or implant delivery tools.

The first end effector 1716 is operable with one or more tools 1712, such as a suture needle driver, grasping instrument, and/or a flexible endoscope. The second end effector 1718 is configured to manipulate a sheath or catheter 1710, which may contain multiple lumens for guiding the tools 1712 (e.g., implant delivery tools) toward the target anatomical site.

An electromagnetic (EM) generator 1714 is integrated into the robotic surgical system 1700 to produce an EM field detectable by sensors embedded within the implant delivery tool or the implant itself. For example, an EM sensor may be positioned on the distal tip of the driver tool or on the implantable device to provide real-time positional and orientation data. The EM generator 1714 may be embedded within the operating table 1715 or placed beneath the patient 1711 via a dedicated pad.

The robotic arms 1702 and 1704 are precisely controlled to maintain axial alignment between the catheter 1710 and the tools 1712. This ensures that the proximal end of the catheter remains distal to the proximal ends of the tools, facilitating seamless instrument (e.g., AIMD) deployment.

In one embodiment, the first robotic arm 1702 introduces the catheter 1710 through a designated access point—such as a percutaneous incision or anatomical conduit—and advances it toward the target site. The second robotic arm 1704 then deploys the tools 1712 through the catheter to perform tasks such as dissection, device (e.g., AIMD) anchoring, or suturing.

The robotic arms may be actuated to move the catheter and tools axially and rotationally under the guidance of a surgeon operating from a control console. This enables dynamic adjustment during implantation procedures.

During the navigation phase, the catheter 1710 and tools 1712 are advanced into the patient 1711, with the tools extending beyond the catheter's distal tip 1713 to reach the implantation site. Alternative navigation methods may include guide wire-assisted advancement through a working channel.

Surgeons may utilize multimodal imaging—such as fluoroscopy, CT, MRI, or endoscopic video—to guide the robotic system during device placement. The tools 1712 (e.g., AIMD) are deployed through longitudinally aligned channels within the catheter to perform implantation, fixation, and any adjunct procedures.

The robotic arms 1702 and 1704 may include three joints 1701 and three arm segments 1705, although configurations with more or fewer joints and segments are also contemplated to accommodate anatomical variability and procedural complexity.

In one aspect, the present disclosure relates to robotic systems and methods for the precise, non-invasive placement of an Active Wearable Medical Device (AWMD) on the external surface of a subject's body. Unlike implantable drug delivery devices, the AWMD is configured for wearable, skin-mounted use and provides transdermal or subcutaneous therapeutic delivery without surgical implantation.

The robotic system comprises a robotic actuator, a control unit, and a patient-specific sensor module configured to optimize placement of the AWMD on anatomically suitable skin regions. The robotic actuator may include one or more programmable robotic arms with articulated joints and precision end-effectors designed for manipulating and affixing wearable medical devices. In some embodiments, the actuator includes embedded force sensors to regulate the applied pressure during placement, ensuring optimal adhesion without patient discomfort.

The sensor module is configured to collect anatomical and physiological data from the patient's body surface. This may include skin texture, surface curvature, tissue compliance, or underlying vasculature mapping via optical, infrared, ultrasound, or tactile sensing modalities. The collected data is transmitted to the control unit, which analyzes the surface and generates a placement control signal to guide robotic movement.

The control unit uses the sensor data to identify a therapeutically optimal site for device placement based on drug absorption profiles, avoidance of sensitive regions, rotation of application sites, and prior dosing history. Once the placement site is determined, the robotic actuator positions the AWMD on the selected region. The device is affixed using integrated medical-grade adhesives or mechanical docking features, with feedback verification from sensors or imaging systems.

The AWMD comprises a drug chamber, a permeability module for ingress flow of a fluid and osmotic pressure generation, an osmotic agent chamber, a piston-based ejection mechanism, a one-way flow control valve, displacement sensors for real-time piston monitoring, and electronic circuitry for regulating drug delivery. The AWMD further includes a machine learning model for alert triggering when dosing exceeds predefined thresholds and is externally worn on the body.

Robotic placement enhances device alignment, ensures repeatable positioning, and reduces manual handling errors. The system may allow dynamic adjustment based on patient body morphology or posture, supporting both initial placement and repositioning. Real-time feedback may confirm successful attachment, verify device function (e.g., fluid priming, sensor calibration), and initiate post-placement diagnostics.

This embodiment provides clinical benefits, including improved therapeutic precision, reduced device misalignment, consistent drug delivery performance, and enhanced user comfort. Additionally, the system supports safe and efficient operation in outpatient or home care settings, eliminating the need for invasive procedures while maintaining the therapeutic effectiveness of a controlled delivery platform.

Figure 18:
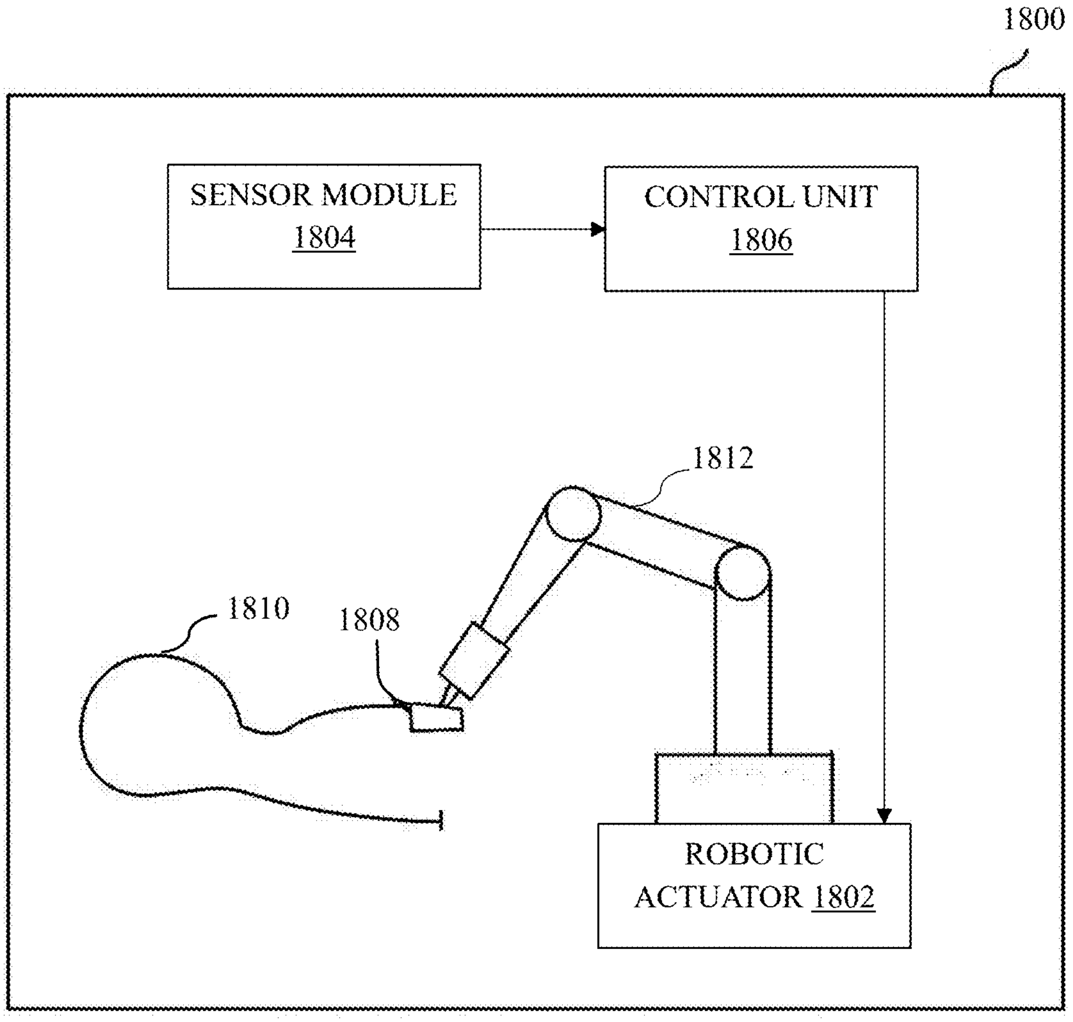
FIG. 18 illustrates a system configured for robotic placement of an Active Wearable Medical Device (AWMD) onto a patient's body, according to one or more embodiments.

FIG. 18 illustrates a system 1800 configured for robotic placement of an Active Wearable Medical Device (AWMD) 1808 onto a patient's body, according to one or more embodiments. The system 1800 is operable to identify an anatomically and therapeutically optimized placement site and to execute device application using robotic actuation. The system 1800 comprises a robotic actuator 1802, a sensor module 1804, and a control unit 1806, which are operatively coupled to form a closed-loop control architecture.

The robotic actuator 1802 is configured to position and affix the AWMD 1808 to the patient's skin. The robotic actuator 1802 may include one or more robotic arms 1812, end-effectors, articulated joints, or linear guides capable of high-precision manipulation. In some embodiments, the robotic actuator 1802 further includes force or pressure sensors to regulate affixation force during placement.

The sensor module 1804 is configured to acquire anatomical data from the target region on the patient's body 1810. The anatomical data may include skin texture, subcutaneous tissue profiles, or vascular structures, obtained using imaging or sensing modalities including ultrasound, infrared imaging, optical coherence tomography, or tactile sensing. The sensor module 1804 may be integrated with the robotic actuator or implemented as a separate scanning unit.

The control unit 1806 is operatively coupled to both the robotic actuator 1802 and the sensor module 1804. The control unit 1806 is configured to analyze the anatomical data and identify a suitable placement region based on therapeutic criteria, including drug absorption characteristics, avoidance of vasculature, site rotation history, and tissue compliance. The control unit 1806 generates a placement control signal based on this analysis.

In response to the control signal, the robotic actuator 1802 is configured to maneuver and affix the AWMD 1808 onto the identified region. In some embodiments, affixation may be verified via real-time feedback from embedded sensors or imaging systems.

The AWMD 1808 may include, but is not limited to, transdermal patches, microneedle arrays, or wearable infusion pumps, and may be configured for either single-use or reusable operation. The system 1800 thus enables safe, precise, and patient-specific device application, improving therapeutic efficacy and minimizing risk of misplacement.

In another aspect, Active Implantable Medical Devices (AIMDs) are assembled from multiple components manufactured at different facilities. There is a need to track each module throughout the manufacturing and supply chain. This creates a significant risk of counterfeit or mismatched components being introduced into the supply chain. Such incidents can compromise patient safety, result in regulatory non-compliance, and lead to device failure.

There is also a need to ensure the authenticity of modules and components to prevent the introduction of counterfeit parts and guarantee that only verified modules are used in the final assembly. Currently, there is no reliable, non-toxic, and biocompatible method to authenticate each module's origin and integrity, track components throughout manufacturing and assembly, and prevent unauthorized modules from being inserted into final devices.

The solution must function in high-assurance biomedical manufacturing environments and avoid introducing toxic substances that could later impact patient safety.

This work may require a hardware-based authentication system. Such a system could be embedded in different modules and components as needed. In one embodiment, the hardware-based authentication system is present in all components and modules. For example, components or modules may include built-in chips with tamper resistance, or even quantum-based ID systems. Each module may carry a unique, verifiable ID (e.g., a physical unclonable function or encrypted tag).

The hardware-based authentication system may include a tracking capability that can detect tampering or substitution. It is important to note that materials used for tracking (e.g., microchips, sealants, embedded quantum markers) must be non-toxic and biocompatible. Environmental robustness can be achieved using techniques such as hermetic sealing, nitrogen flushing, or vacuum isolation during the manufacturing process.

The term "biocompatible" refers to materials that do not trigger significant inflammation or immune rejection in a patient's body, do not release toxic substances, and maintain their function safely over time in the body's environment.

In one embodiment, the embedded identifier, chip, or similar hardware component could be designed to degrade upon tampering. It is also possible for hardware components encoding traceable, quantum-sensitive materials to lose functionality if exposed.

In another embodiment, the modules or components can be coated with temporal resistance-like coating (TRC) materials to monitor chain-of-custody. A temporal resistance-like coating is a special type of material layer or film designed to degrade, change, or lose effectiveness in a controlled way over time or in response to environmental conditions such as heat, moisture, pH, light, or mechanical stress. It temporally resists these changes—meaning it maintains integrity for a specific period or under certain conditions—and then deliberately breaks down or alters.

In hardware security mechanisms, a TRC coating can serve as an anti-tamper layer on chips, such as resin layers that degrade when exposed to heat or UV light, destroying circuits if someone attempts to open or probe them.

In an embodiment, an active implantable medical device (AIMD) along with other components, comprising a plurality of modules, wherein one or more modules comprises: a) a hardware-based authentication element uniquely identifying the module; b) a biocompatible encapsulation enclosing the authentication element; and c) a module tracking system configured to verify identity and integrity of the module prior to final assembly.

In an embodiment, the hardware-based authentication element comprises a physical unclonable function (PUF), RFID tag, or optically encoded microstructure.

In an embodiment, the biocompatible encapsulation includes a hermetic seal, vacuum chamber, or nitrogen-filled cavity.

In an embodiment, the module tracking system comprises a handheld or assembly-line reader configured to authenticate the module using a cryptographic handshake or physical signal.

In an embodiment, any tampering with the authentication element renders the module inoperable or flags it as invalid for assembly.

Figure 19:
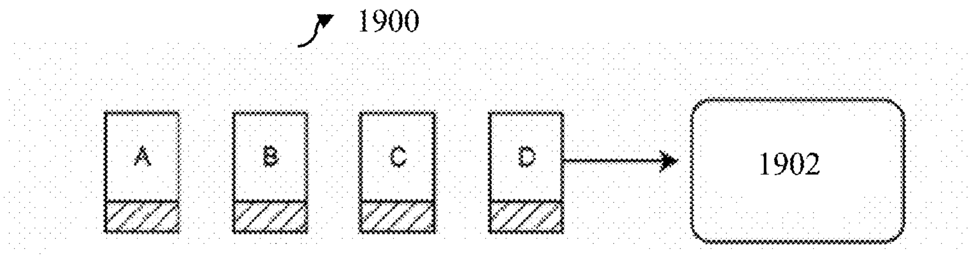
FIG. 19 represents an exemplary AIMD System, according to one or more embodiments.

FIG. 19 represents an exemplary AIMD System 1900, according to one or more embodiments. The AIMD System 1900 comprises individual modules labeled as A-D having an embedded unique ID or authentication marker and connected to a central control system 1902 that verifies module identity before final assembly. Although the example shows four modules, an AIMD system may include one, two, three, or more modules. It is also possible for each module to have its own control system to verify its authenticity. Alternatively, two or more modules may share a common control system to verify authenticity. Further, one or more modules with individual control systems can be connected to a single, centralized control system.

Figure 20:
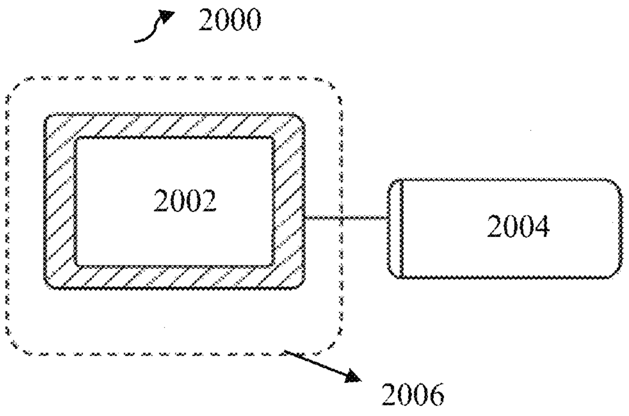
FIG. 20 illustrates an exemplary module authentication mechanism, according to one or more embodiments.

FIG. 20 illustrates an authentication mechanism 2000, according to one or more embodiments. One or more modules contain an embedded authentication element, such as a chip or material tag 2002. A reader interface 2004 at the assembly line can verify the identity through mechanisms such as secure hardware handshakes or optical signatures. The authentication element can be surrounded by biocompatible packaging 2006, such as a tamper-evident seal. An optional polymer seal (not shown) may provide additional environmental shielding.

Figure 21:
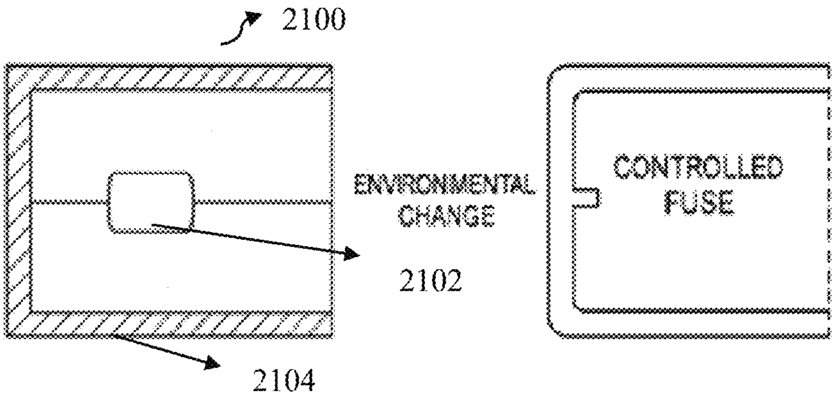
FIG. 21 shows an authentication mechanism in a module, according to one or more embodiments.

FIG. 21 shows an authentication mechanism 2100 in a module, according to one or more embodiments. One or more modules may contain an embedded authentication element such as a chip or material tag 2102 made of TRC-like material. The authentication element can be surrounded by a TRC 2104. If tampering occurs or a change in environment is detect, the TRC degrades, breaking the seal and causing the circuit to fuse, which results in the failure of the reader interface (not shown) to retrieve the data.

In one embodiment, the active implantable medical device (AIMD) or its individual modules may be enclosed within a non-toxic sleeve or encapsulation to ensure biocompatibility and compliance with international safety standards. For example, the device may be manufactured in accordance with the European Union's Restriction of Hazardous Substances (RoHS) Directive, which limits the use of six hazardous materials in electrical and electronic equipment: Cadmium (Cd) to a maximum of 0.01% by weight, and Lead (Pb), Mercury (Hg), Hexavalent Chromium (Cr VI), Polybrominated Biphenyls (PBB), and Polybrominated Diphenyl Ethers (PBDE) each to a maximum of 0.1% by weight. Comparable regulations exist in other jurisdictions, including China RoHS, Japan RoHS (J-MOSS), Taiwan RoHS, South Korea RoHS, and Singapore RoHS. In the United States, while there is no federal RoHS equivalent, several states, such as California, have enacted similar restrictions. To further enhance security and traceability, the AIMD system may incorporate supply chain tracking technologies such as blockchain for immutable transaction records, RFID and NFC for real-time authentication, IoT sensors for environmental monitoring, and enterprise resource planning (ERP) systems for integrated traceability across manufacturing stages. These features collectively ensure that only verified, non-toxic, and traceable components are used in the final assembly of the AIMD, thereby enhancing patient safety and regulatory compliance.

In one aspect, the present disclosure provides a system and method for the controlled self-destruction or permanent deactivation of an AIMD upon reaching its end-of-life (EOL), particularly after the conclusion of a drug delivery cycle. The purpose of the self-destruction mechanism is to prevent illicit reuse, reverse engineering, and unsafe reimplantation of the device, while maintaining safety for patients and healthcare providers.

In one embodiment, the active implantable medical device (AIMD) comprises a self-destruction mechanism configured to be activated upon completion of a therapeutic cycle, such as the full discharge of a drug reservoir. The self-destruction mechanism is designed to render the AIMD permanently inoperable, thereby preventing reuse, reverse engineering, or unauthorized reimplantation, while ensuring biocompatibility and patient safety.

The self-destruction mechanism may be triggered by a control signal generated by a microcontroller or sensor module upon detection of a terminal event, such as the piston reaching its end-of-stroke position. The control signal initiates one or more destruct modalities.

Figure 22:
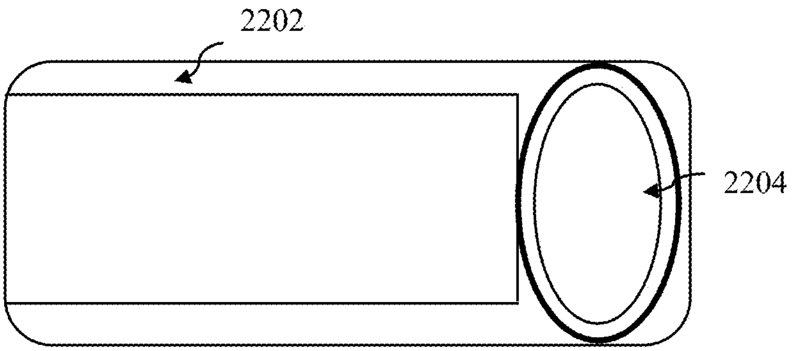
FIG. 22 illustrates a schematic cross-sectional view of an active implantable medical device comprising self-destruction mechanism, according to one or more embodiments.

FIG. 22 illustrates a schematic cross-sectional view of an Active Implantable Medical Device 2202 comprising self-destruction mechanism 2204.

In one embodiment, the AIMD includes a temporal resistance coating applied to one or more structural or functional components. The TRC is composed of a material that remains stable under physiological conditions but degrades upon exposure to specific environmental stimuli, such as atmospheric oxygen, ultraviolet or visible light, elevated temperature, or pH changes. Upon explantation, the TRC undergoes a controlled degradation process, leading to the disintegration of critical components such as the housing, circuitry, or interconnects.

Figure 23:
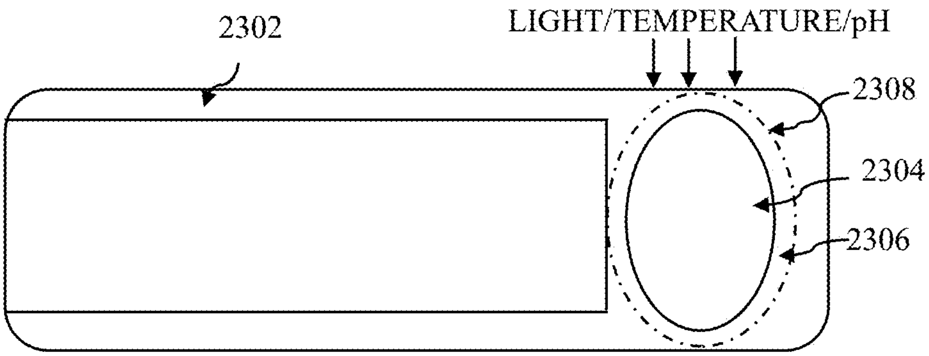
FIG. 23 illustrates a schematic view of a self-destruction mechanism incorporated within an Active Implantable Medical Device (AIMD), according to one or more embodiments.

FIG. 23 illustrates a schematic view of a self-destruction mechanism incorporated within an Active Implantable Medical Device (AIMD), specifically highlighting the role of a Temporal Resistance Coating (TRC) in facilitating controlled device deactivation. The outermost boundary of the FIG. 2302 represents the AIMD itself, shown as a sealed, biocompatible enclosure optimized for subcutaneous implantation. Housed within this enclosure is a designated internal module 2304, which may contain essential components such as microelectronic circuits, data storage elements, or structural elements integral to the device's therapeutic or functional operation. Encasing this module is the TRC layer 2306, composed of environmentally responsive material designed to remain inert during normal in vivo operation. However, the TRC is engineered to undergo degradation when exposed to specific environmental triggers such as atmospheric oxygen, UV or visible light, or shifts in pH—typically occurring upon device explantation or accidental exposure. The figure includes directional arrows 2308 entering the AIMD, symbolizing environmental intrusion (e.g., air, fluid, or radiation) that activates the TRC breakdown. This degradation is visually represented by fragmentation or disintegration of the coating layer, which in turn initiates the irreversible destruction, disconnection, or deactivation of the encapsulated module.

In another embodiment, the AIMD comprises a microfabricated fuse circuit integrated into the electronic control system. Upon receiving the end-of-life signal, the fuse is selectively blown, thereby irreversibly severing electrical connectivity within the device. The fuse may be configured to disrupt power delivery, data communication, or control signal pathways, effectively disabling the device's operational capabilities.

Figure 24:
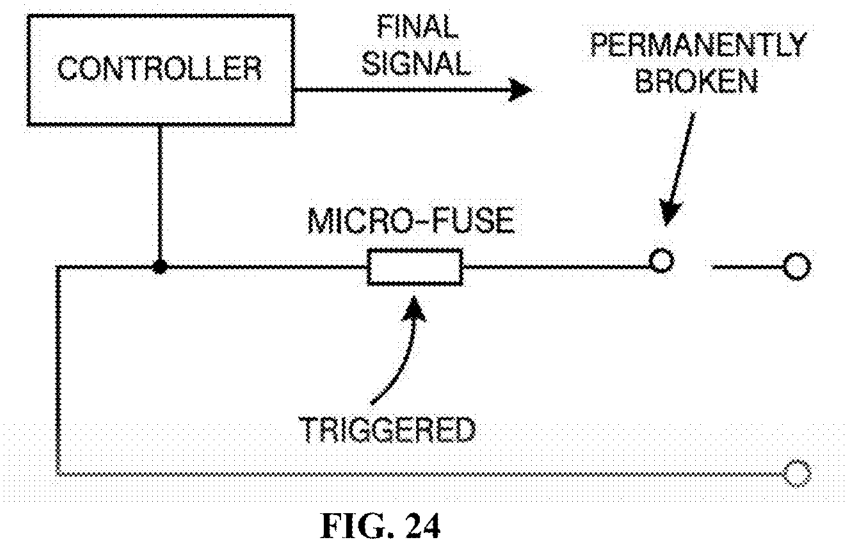
FIG. 24 presents a schematic representation of a circuit-based self-destruction mechanism integrated within an Active Implantable Medical Device (AIMD), according to one or more embodiments.

FIG. 24 presents a schematic representation of a circuit-based self-destruction mechanism integrated within an Active Implantable Medical Device (AIMD), illustrating the use of a micro-fuse element to achieve permanent deactivation of the device's electronic functions after completion of its therapeutic role. The diagram depicts a simplified internal circuit layout, featuring a controller module tasked with monitoring the device's operational status. Embedded along the active electrical pathway between the power source and the core electronics is a micro-fuse, which serves as a critical control point. Upon detection of an end-of-life condition—such as full depletion of the drug reservoir or complete displacement of a piston—the controller initiates a final shutdown sequence by transmitting an activation signal to the micro-fuse. Once triggered, the fuse irreversibly severs the electrical connection, thereby disabling power and/or communication lines linked to the essential electronic subsystems. This action results in the permanent and non-reversible deactivation of the AIMD, preventing any possibility of reuse, recharging, or reverse engineering. Arrows in the schematic indicate the direction of signal transmission from the controller to the fuse and depict the break in the circuit that follows.

In yet another embodiment, the AIMD includes components fabricated from environmentally responsive materials that undergo structural breakdown upon exposure to non-physiological conditions. For example, materials may be selected to degrade in the presence of ambient air, moisture, or specific chemical agents encountered during explantation or sterilization. This degradation may result in fragmentation, delamination, or dissolution of internal components, thereby rendering the device non-functional.

In a further embodiment, the AIMD incorporates quantum-state-dependent subsystems that rely on quantum confinement or entanglement for functionality. Upon exposure to environmental transitions—such as changes in electromagnetic fields, pressure, or temperature—the quantum state decoheres, resulting in irreversible loss of function. This mechanism ensures that the internal architecture of the AIMD becomes scrambled or unreadable, thereby preventing reverse engineering.

The self-destruction mechanism is configured to operate without generating heat, mechanical shock, or toxic byproducts. The degradation process is gradual and confined within the structural boundaries of the AIMD. In some embodiments, the device may include a signaling mechanism, such as a low-energy RF beacon or visual indicator, to notify clinical personnel that the device has entered or completed the self-destruction phase.

In one embodiment, the active implantable medical device (AIMD) is further configured to detect whether the therapeutic agent contained within the device has exceeded its designated shelf life and, upon such detection, to render itself permanently inoperable. This functionality may be achieved through the integration of one or more technologies including, but not limited to: embedded RFID (Radio Frequency Identification) or NFC (Near Field Communication) tags within the medication packaging to store expiration data; dynamic codes such as QR codes or barcodes linked to a centralized database containing shelf-life information; environmental monitoring sensors capable of tracking storage conditions such as temperature, humidity, and light exposure to dynamically assess degradation risk; and integrated chemical sensors capable of detecting changes in the medication's composition indicative of expiration. Upon confirmation of expiration, the device initiates a self-destruction sequence to prevent administration of ineffective or unsafe medication. Additionally, the AIMD may incorporate an advanced self-diagnostic system designed to ensure operational integrity and patient safety. This system includes error detection algorithms, self-calibration routines, real-time monitoring of critical components, usage tracking, and wear-and-tear analysis to accurately determine the device's end-of-life. If an uncorrectable error is detected, the device automatically initiates a shutdown sequence, rendering itself inoperable. The system may further include a communication interface with wireless connectivity for remote monitoring, data logging, and transmission of diagnostic information. Power management features such as battery health monitoring, energy optimization, and emergency power-off capabilities are also included. A user interface may be provided with an intuitive display, interactive controls, and visual indicators—such as color changes—to alert users to device status or medication degradation. These features collectively ensure that only safe, effective, and authenticated devices are deployed, thereby enhancing patient safety and regulatory compliance.

This destruct mechanism ensures single-use integrity of the AIMD, enhances security against tampering, and supports regulatory compliance by preventing unauthorized reuse or analysis of the device post-explantation.

In an aspect, the disclosure relates to relates to a medical system designed for intelligent, automated drug dose titration based on real-time physiological data. This enables precise, adaptive drug dosing that responds instantly to the patient's needs, maximizing efficacy and safety throughout therapy. The system comprises a drug delivery pump, which may be configured as either an implantable or wearable unit, comprising a drug reservoir for storing a therapeutic agent and a drug dispensing mechanism that controllably administers the agent into the patient. Real-time physiological data transforms PK/PD modeling from a static prediction tool into a dynamic, continuously learning system. One or more physiological sensors are integrated with the system and are configured to measure drug concentration in the patient's interstitial fluid, which serves as a proxy for plasma drug levels. Sensor data is processed by a control processor, which comprises memory for storing historical sensor readings and patient-specific treatment parameters, and an artificial intelligence (AI) engine capable of executing dose titration algorithms. The AI engine estimates key pharmacokinetic and pharmacodynamic (PK/PD) parameters, comprising the absorption rate constant (ka), elimination rate constant (ke), and minimum effective concentration (Cmin), using predictive modeling techniques. Based on these parameters, the AI engine determines appropriate dosage adjustments and generates control signals to actuate the drug dispensing mechanism. The AI engine iteratively updates its predictive model based on feedback from subsequent sensor readings, enabling continuous optimization of drug therapy.

In some implementations, the pump may comprise dual reservoirs to facilitate combination therapies, with the AI engine dynamically determining not only the dosage but also the selection and sequencing of drugs. The system may further incorporate external communication interfaces, allowing integration with smartphones, hospital systems, or cloud-based medical records for remote monitoring, clinician oversight, and software updates. A patient-specific baseline model may be initialized at the time of implantation or application, using genomic, proteomic, or clinical data to individualize the therapy from the outset.

In some embodiments, following each drug titration event, the system re-evaluates the pharmacokinetic and pharmacodynamic profile under the updated dosing conditions. The artificial intelligence engine reassesses the parameters such as absorption rate, elimination rate, and effective concentration thresholds to refine the predictive model. This ongoing reassessment ensures that the drug delivery strategy remains aligned with the patient's dynamic physiological state.

In an embodiment, the system comprises a dedicated safety module capable of detecting anomalous or unsafe operating conditions and initiating corrective actions such as halting drug delivery, alerting medical personnel, or activating secure override protocols. Additional safety features comprise a clinician override interface, a fail-safe shutoff mechanism that disables drug administration in response to specific threshold events, and an end-of-life (EOL) self-deactivation protocol triggered by battery depletion, reservoir exhaustion, or sensor degradation. Furthermore, redundancy in sensor data processing and constrained learning rates are implemented to prevent unsafe or erratic dose escalations. The disclosed system is particularly advantageous in managing chronic diseases such as diabetes, cancer, Parkinson's disease, and epilepsy, where precise, responsive, and individualized drug delivery is critical to therapeutic success.

An embodiment relates to an active implantable medical device (AIMD) system comprising: a) a plurality of modules configured to perform therapeutic and/or diagnostic functions; and b) at least one of said modules comprising: i. a hardware-based authentication element configured to uniquely identify the module; ii. a biocompatible encapsulation enclosing the authentication element; and iii. a module tracking system configured to verify the identity and integrity of the module prior to final assembly of the AIMD; wherein the authentication element is further configured to render the module inoperable or mark it as invalid for assembly upon detection of tampering or substitution.

In an embodiment, the hardware-based authentication element comprises a physical unclonable function (PUF), a radio-frequency identification (RFID) tag, or an optically encoded microstructure.

In another embodiment, the biocompatible encapsulation comprises a hermetically sealed enclosure, a vacuum-isolated cavity, or a nitrogen-filled chamber.

In yet another embodiment, the module tracking system comprises a reader configured to authenticate the module via a cryptographic handshake or by detecting a physical signal from the authentication element.

In yet another embodiment, the authentication element is configured to degrade or become unreadable upon exposure to environmental conditions indicative of tampering.

In yet another embodiment, the authentication element is embedded within a temporal resistance coating (TRC) configured to degrade upon exposure to heat, light, pH, or mechanical stress.

In yet another embodiment, the authentication element comprises a quantum-sensitive material configured to lose functionality upon exposure to environmental transitions.

In yet another embodiment, each module comprises an individual control system configured to verify its own authenticity.

In yet another embodiment, two or more modules share a common control system configured to verify the authenticity of each module prior to final assembly.

In yet another embodiment, the authentication element is enclosed within a tamper-evident seal or a polymer-based environmental shield.

An embodiment relates to an active implantable medical device (AIMD) comprising: a drug delivery subsystem configured to administer a therapeutic agent to a patient; a sensor or controller configured to detect completion of a therapeutic delivery cycle based on one or more terminal event conditions associated with the drug delivery subsystem; and a self-destruction mechanism operatively coupled to the controller and configured to be irreversibly activated in response to detection of the terminal event condition, wherein the self-destruction mechanism is configured to permanently disable at least one functional component of the AIMD, thereby preventing reuse, reverse engineering, or unauthorized reimplantation.

In an embodiment, the terminal event condition comprises full depletion of the therapeutic agent or a piston reaching its end-of-stroke position within the drug delivery subsystem.

In yet another embodiment, the self-destruction mechanism comprises a temporal resistance coating (TRC) applied to one or more internal or external components of the AIMD, the TRC being stable under physiological conditions and configured to degrade upon exposure to environmental stimuli selected from atmospheric oxygen, ultraviolet or visible light, pH change, moisture, or temperature fluctuation.

In yet another embodiment, degradation of the temporal resistance coating results in mechanical or electrical disintegration of a critical component, thereby causing irreversible loss of device functionality.

In yet another embodiment, the self-destruction mechanism comprises a micro-fabricated fuse circuit electrically connected to the core electronics of the device, the fuse being configured to receive an activation signal from the controller and, upon activation, to permanently sever one or more electrical pathways associated with power delivery or data communication.

In yet another embodiment, the self-destruction mechanism comprises a structural component fabricated from an environmentally responsive material configured to undergo irreversible breakdown upon exposure to non-physiological conditions encountered during explantation or sterilization.

In yet another embodiment, the self-destruction mechanism comprises one or more quantum-state-dependent components whose functionality is based on quantum confinement, coherence, or entanglement, and wherein exposure to environmental transitions such as electromagnetic interference or pressure change causes decoherence and irreversible loss of function.

In yet another embodiment, activation of the self-destruction mechanism is accompanied by a signaling event selected from: (a) emission of a low-energy radiofrequency (RF) beacon; (b) activation of a visual indicator such as an LED; or (c) a magnetically detectable change in state, to notify clinical personnel of device deactivation.

In yet another embodiment, the self-destruction mechanism is biocompatible and non-toxic, and is configured to avoid introducing thermal, mechanical, or chemical hazards to the patient or surrounding tissue upon activation.

In yet another embodiment, the controller comprises a microcontroller integrated with memory and firmware logic configured to perform device state monitoring, detect terminal event conditions, and initiate timed or conditional triggering of the self-destruction mechanism.

An embodiment relates to a system comprising a robotic manipulator comprising a first robotic arm configured to access a target anatomical site within a body of a mammal; an active implantable medical device (AIMD) comprising a biocompatible housing, a drug chamber, a piston, an electronic module, and a channel port; a channel operatively coupled to the channel port and configured to deliver a therapeutic agent to the target anatomical site; and an imaging and navigation system configured to guide the robotic manipulator; and wherein the robotic manipulator is configured to create a pocket, place the AIMD into the pocket, route the channel to the target anatomical site, and secure the AIMD and the channel in place.

In an embodiment, the channel comprises at least one of a bacterial filter, a check valve, and a flow control regulator.

In yet another embodiment, the further comprises a second robotic arm configured to manipulate a sheath for routing the AIMD toward the target anatomical site.

In yet another embodiment, the imaging and navigation system comprises modality of at least one of fluoroscopy, computed tomography (CT), magnetic resonance imaging (MRI), and ultrasound.

In yet another embodiment, the robotic manipulator comprises end-effectors configured for dissection, implantation, and suturing.

In yet another embodiment, the system further comprises an electromagnetic generator and a sensor configured to track a position of one of the AIMD and a surgical tool during implantation.

In yet another embodiment, the robotic manipulator is configured to connect one or more components of the AIMD and deliver a test bolus to verify channel patency and function of the one or more components.

In yet another embodiment, the channel is configured to access the target anatomical site selected from at least one of an intrathecal space, a peritoneal cavity, and an intravascular compartment.

In yet another embodiment, the robotic manipulator operates under closed-loop control to maintain alignment between the channel and an implant delivery tool.

In yet another embodiment, the robotic manipulator is actuated to perform minimally invasive dissection through one or more incisions under real-time imaging guidance.

An embodiment relates to a system comprising a robotic actuator comprising a robotic arm with at least one articulated joint and an end-effector configured to affix an active wearable medical device (AWMD) onto a skin of a body of a mammal; a sensor module configured to collect anatomical data from a target region on the body; and a control unit operatively coupled to the robotic actuator and the sensor module; and wherein the control unit analyzes the anatomical data to identify an optimized placement site within the target region and generates a control signal to guide the robotic actuator to affix the AWMD at the optimized placement site.

In an embodiment, the sensor module acquires at least one of skin texture, surface curvature, tissue compliance, and subcutaneous vasculature data.

In yet another embodiment, the robotic actuator comprises one or more embedded force sensors configured to regulate affixation pressure.

In yet another embodiment, the AWMD comprises a drug chamber, an osmotic agent chamber, a piston, a valve module, an electronic module, and a machine learning model.

In yet another embodiment, the control unit selects the optimized placement site based on at least one of drug absorption efficiency, prior site usage, and avoidance of sensitive regions.

In yet another embodiment, the robotic actuator is configured to reposition the AWMD based on at least one of patient posture, dosing history, and a feedback from the sensor module.

In yet another embodiment, system further comprises a feedback verification module configured to detect successful adhesion and initiate device diagnostics.

In yet another embodiment, the AWMD is selected from at least one of a microneedle array, a transdermal patch, and a wearable infusion pump.

In yet another embodiment, the machine learning model of the AWMD is configured to trigger alerts upon exceeding dosage thresholds.

In yet another embodiment, the robotic actuator, the sensor module, and the control unit operate in a closed-loop control system for precision-guided placement and verification.

An embodiment relates to a medical system configured for automated drug dose titration in a patient, the system comprising a drug delivery pump comprising a drug reservoir configured to store a therapeutic agent and a drug dispensing mechanism operatively coupled to the drug reservoir and configured to controllably release the therapeutic agent into the patient; one or more physiological sensors configured to measure a drug concentration in interstitial fluid of the patient and generate sensor data corresponding to the measured drug concentration; a control processor operatively coupled to the one or more physiological sensors and the drug dispensing mechanism, the control processor comprising a memory storing historical sensor data and patient-specific parameters and an artificial intelligence engine configured to process the sensor data to estimate pharmacokinetic and pharmacodynamic parameters of the therapeutic agent, the parameters including at least an absorption rate constant, an elimination rate constant, and a minimum effective concentration, determine a current dosage adjustment based on the pharmacokinetic and pharmacodynamic parameters using a predictive model, generate a control signal to activate the drug dispensing mechanism to deliver the adjusted dosage, and iteratively update the predictive model based on feedback from subsequent sensor data; wherein the system further comprises one or more safety modules configured to detect anomalous or unsafe conditions and initiate one or more safety responses selected from halting drug delivery, sending alerts to a caregiver, or initiating a secure override protocol.

In an embodiment, the artificial intelligence engine comprises a reinforcement learning model configured to learn optimal dosage strategies by maximizing therapeutic efficacy over time.

In yet another embodiment, the artificial intelligence engine further comprises a supervised learning model trained on historical patient data and clinical outcomes to predict adverse drug reactions.

In yet another embodiment, the safety module includes an end-of-life deactivation circuit configured to detect exhaustion of the drug reservoir or battery power and irreversibly disable the drug dispensing mechanism.

In yet another embodiment, the drug dispensing mechanism comprises a microfluidic or piezoelectric pump configured for microliter-precision actuation based on the control signal from the control processor.

In yet another embodiment, the system further comprises a clinician override interface configured to receive override commands from an external device via a secure wireless protocol and temporarily or permanently disable the artificial intelligence-driven dosage control.

In yet another embodiment, the control processor is configured to stratify patient response data into therapy response clusters using unsupervised learning algorithms and modify treatment regimens accordingly.

In yet another embodiment, the control processor receives patient-specific initialization parameters including genetic, proteomic, or demographic data to personalize the starting dose model.

In yet another embodiment, the system integrates with a remote server or electronic medical record system to transmit therapy data for clinical monitoring and receive software or model updates for the artificial intelligence engine.

An embodiment relates to a computer-implemented method for automated drug dose titration in a patient, the method comprising: receiving, from one or more physiological sensors, real-time data corresponding to a concentration of a therapeutic agent in interstitial fluid of the patient; estimating, by a control processor comprising an artificial intelligence engine, pharmacokinetic and pharmacodynamic parameters based on the received data, the parameters including at least an absorption rate constant, an elimination rate constant, and a minimum effective concentration; determining, by the artificial intelligence engine, a dose adjustment based on the estimated parameters using a predictive model; generating a control signal to actuate a drug dispensing mechanism of a drug delivery pump to deliver the adjusted dosage to the patient; and updating the predictive model based on feedback derived from subsequent physiological sensor data to optimize future dosing decisions.

In an embodiment, the method further comprises initializing a patient-specific baseline model prior to first drug administration, wherein the model is derived from genomic, proteomic, or clinical diagnostic data.

In yet another embodiment, the artificial intelligence engine comprises a reinforcement learning model that continuously improves dosage selection based on cumulative therapy outcomes.

In yet another embodiment, the artificial intelligence engine comprises a supervised learning model trained to predict adverse drug reactions based on historical patient data and treatment outcomes.

In yet another embodiment, determining the dose adjustment comprises selecting and sequencing drug delivery from a plurality of drug reservoirs configured in the drug delivery pump.

In yet another embodiment, the method further comprises detecting, by a safety module, an anomalous condition comprising one or more of: excessive drug accumulation, sensor failure, or patient non-responsiveness; and halting drug administration in response to the detection.

In yet another embodiment, the method further comprises receiving a clinician override command from an external device, and temporarily disabling automated dose titration control in response to the override command.

In yet another embodiment, the method further comprises triggering a fail-safe shutoff or end-of-life deactivation procedure when the system detects at least one of battery depletion, reservoir exhaustion, or sensor degradation.

In yet another embodiment, the drug dispensing mechanism is a microfluidic or piezoelectric pump configured for microliter-precision drug delivery.

In yet another embodiment, the method further comprises transmitting dosing history and sensor data to a remote server or electronic medical record system for clinical monitoring and software update delivery.

In yet another embodiment, the method further comprises re-evaluating the pharmacokinetic and pharmacodynamic parameters after each dosage titration based on updated physiological sensor data, wherein the re-evaluation comprises recalculating at least the absorption rate constant, the elimination rate constant, and the minimum effective concentration to refine subsequent dosage decisions.

It should be noted that the flowchart and the suggested time limits and parameters are meant to be exemplary, and that there could be other measures or criteria used in order to maximize safety and accuracy.

REFERENCE SIGNS LIST

102, 202, 302, 602, 702, 802—Drug chamber
104, 204, 304, 604, 704, 804—Drug
106, 206, 306, 606, 706, 806—Motor chamber
108, 208, 308, 608, 708, 808—Housing
110, 210, 310, 610, 710, 810—Motor
112, 212, 312, 612, 712, 812—Driving component
114, 214, 314, 614, 714, 814—Piston
116, 216, 316, 616, 716, 816—Electronic Module
117, 217, 317, 617, 717, 817, 1804—Sensor Module
118, 218, 318, 618, 718, 818—Orifice
220, 320, 620, 720, 820—Check Valve
622—Semipermeable membrane
724—provisions
826—gas
502—external enclosure
502*a*—second perforated end
504—valve
506—piston assembly
508—motor and shaft assembly
508*a*—gear
510—electronics unit
512—submersible pump assembly
514—sliding spacer
518—drug chamber
624—hollow fiber membrane
626—flexible fibers
628—casing
630—second end
902, 904, 906—Method steps
1001—Computer system
1002—Non-transitory computer readable medium
1004—processor
1005, 1007, 1009—Steps
1100, 1200, 1300, 1400, 1500—wearable drug delivery system
1600—drug delivery system
1102, 1202, 1302, 1402, 1502, 1602, 1808—active wearable medical device (AWMD)
1202*a*, 1302*a*, 1402*a*, 1502*a*—adhesive layer
1104, 1204, 1304, 1404, 1504, 1604—drug outlet
1106, 1206, 1306, 1406, 1506—channel
1120, 1220, 1320, 1420, 1520, 1606, 1710—catheter
1108, 1208, 1308, 1408, 1508—fluid chamber
1110, 1210, 1310, 1410, 1510—microneedles
1112, 1212, 1312, 1412, 1512—adhesive layer
1700—robotic surgical system
1701—joints
1702—first robotic arm
1704—second robotic arm
1705—arm segment
1706, 1708—robotic bases
1711—patient
1712—tools
1713—catheter's distal tip
1714—electromagnetic (EM) generator

1715—operating table
1716—first end effector
1718—second end effector
1800—system
1802—robotic actuator
1806—control unit
1810—patient's body
1812—one or more robotic arms
1900—AIMD System
1902—Central control system
2000, 2100—Authentication mechanism
2002, 2102—chip or material tag
2004—reader interface
2006—biocompatible packaging
2104—TRC
2202—Active Implantable Medical Device
2302—outermost boundary
2204—self-destruction mechanism
2304—designated internal module
2306—TRC layer
2308—directional arrows
D—drug

What is claimed is:

1. A system comprising a medical device, the medical device comprising:

at least one drug chamber that comprises a drug;

a motor chamber that comprises a housing, a motor, and a component that drives a piston that is affixed to a first end of the component;

an electronic component that actuates the motor to operate the component and move the piston longitudinally to discharge the drug outside the medical device through one or more orifices;

a semipermeable membrane that allows passive ingress flow of a liquid from a liquid environment outside the medical device to inside of the medical device, thereby generating osmotic pressure to drive the piston longitudinally towards the one or more orifices in addition to actuation of the piston by the motor;

wherein the motor chamber is configured to pressurize a gas within the motor chamber such that pressurization of the gas restricts creation of vacuum within the medical device when the piston moves longitudinally toward the one or more orifices; and wherein the medical device is configured to be or not be implanted in a body of a mammal.

2. The system of claim 1, further comprising a chamber, wherein the chamber comprises the liquid and forms at least a portion of the liquid environment.

3. The system of claim 2, wherein the chamber comprises a rigid reservoir.

4. The system of claim 2, wherein the chamber comprises a hydrogel reservoir.

5. The system of claim 4, wherein the hydrogel reservoir comprises a hydrogel.

6. The system of claim 2, wherein the chamber comprises a microfluidic reservoir.

7. The system of claim 6, wherein the microfluidic reservoir is configured to deliver the liquid to the inside of the medical device.

8. The system of claim 1, wherein the chamber comprises an active operated chamber.

9. The system of claim 2, wherein the chamber comprises a passive operated chamber.

10. The system of claim 1, further comprising a channel that is fluidically coupled to the one or more orifices, wherein the channel is configured to deliver the drug to the outside the medical device, wherein the channel comprises a catheter configured to deliver the drug to a specific anatomical site.

11. The system of claim 10, wherein the catheter is configured for targeted administration of the drug.

12. The system of claim 1, wherein the system comprises an attachment component adapted to secure the system.

13. The system of claim 10, wherein the channel comprises a biocompatible material.

14. The system of claim 1, wherein the system comprises a plurality of drug chambers.

15. The system of claim 14, wherein the system is configured via the electronic component to switch between the plurality of drug chambers for sequential discharge of the drug or combination of discharge of the drug.

16. The system of claim 10, wherein the channel comprises a dissolvable material that naturally dissolves in a body over a period of time.

17. The system of claim 1, wherein the system comprises a real-time imaging and navigation guidance device.

18. The system of claim 17, wherein the real-time imaging and navigation guidance device is configured to aid placement of a catheter and monitor dispersion of the drug in real-time.

19. The system of claim 12, wherein the attachment component comprises an adhesive layer.

20. The system of claim 12, wherein the attachment component comprises one of a mechanical fastener, a wearable strap, a wearable band, and a skin micro-anchor.

* * * * *